US008629240B2

(12) United States Patent
Filfil et al.

(10) Patent No.: US 8,629,240 B2
(45) Date of Patent: Jan. 14, 2014

(54) PEPTIDE LIGANDS FOR CLUSTERIN AND USES THEREOF

(75) Inventors: Rana Filfil, Kanata (CA); Dmitri Tolkatchev, La Prairie (CA); Feng Ni, Pierrefonds (CA); Maureen D. O'Connor-McCourt, Beaconsfield (CA); Anne E. G. Lenferink, Lorraine (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 13/260,676

(22) PCT Filed: Apr. 15, 2010

(86) PCT No.: PCT/CA2010/000566
§ 371 (c)(1), (2), (4) Date: Sep. 27, 2011

(87) PCT Pub. No.: WO2010/118521
PCT Pub. Date: Oct. 21, 2010

(65) Prior Publication Data

US 2012/0121507 A1 May 17, 2012

Related U.S. Application Data

(60) Provisional application No. 61/202,910, filed on Apr. 17, 2009.

(51) Int. Cl.
*A61K 38/00* (2006.01)
*A61P 35/00* (2006.01)
*A61B 5/055* (2006.01)

(52) U.S. Cl.
USPC ......... 530/300; 514/19.3; 514/21.5; 424/9.34

(58) Field of Classification Search
None
See application file for complete search history.

(56) References Cited

U.S. PATENT DOCUMENTS

| | | | | |
|---|---|---|---|---|
| 6,348,185 | B1 * | 2/2002 | Piwnica-Worms | 424/1.69 |
| 2005/0208558 | A1 | 9/2005 | Venter | |

FOREIGN PATENT DOCUMENTS

| | | | | |
|---|---|---|---|---|
| WO | 99/12558 A1 | 3/1999 | | |
| WO | WO 99/12558 | * 3/1999 | | A61K 38/02 |
| WO | WO 99/66046 | * 12/1999 | | C12N 15/49 |
| WO | 2005/080434 | 9/2005 | | |
| WO | 2007/030930 | 3/2007 | | |
| WO | 2007/030930 A1 | 3/2007 | | |
| WO | 2008/049239 | 5/2008 | | |

OTHER PUBLICATIONS

Provenzano et. al. Collagen reorganization at the tumor-stromal interface facilitates local invasion. Published: Dec. 26, 2006. BMC Medicine 2006, 4:38.*

Hawkins et al. Idiotypic Vaccination Against Human B-Cell Lymphoma. Rescue of Variable Region Gene Sequences From Biopsy Material for Assembly as Single-Chain Fv Personal Vaccines. Blood. Jun. 1, 1994;83(11):3279-88.*

Gao et al. In vivo cancer targeting and imaging with semiconductor quantum dots. Nat Biotechnol. Aug. 2004;22(8):969-76.*

International Search Report and Written Opinion of Jul. 15, 2010 for PCT/CA2010/000566.

Berx G, Raspe E, Christofori G, Thiery JP, Sleeman JP. (2007) Pre-EMTing metastasis. Recapitulation of morphogenetic processes in cancer. Clin. Exp, Metastasis. 24: 587.

Gasteiger E. et al. (2005) Protein identification and analysis tools on the ExPASy Server. In: John M. Walker (ed): The Proteomics Protocols Handbook, Humana Press; 571-607.

Gupta GP, Massague J. (2006) Cancer metastasis: building a framework. Cell. 127: 679.

Lau SH, Sham JS, Xie D, Tzang CH, Tang D, Ma N, Hu L, Wang Y, Wen JM, Xiao G, Zhang WM, Lau GK, Yang M, Guan XY. (2006) Clusterin plays an important role in hepatocellular carcinoma metastasis. Oncogene. 25: 1242.

Lenferink AEG, Cantin C, Nantel A, Wang E, Durocher Y, Banville M, Paul-Roc B, Marcil M, Wilson MR & O'Connor-McCourt MD (2009) Transcriptome Profiling of a TGF-beta-induced Epithelial-to-Mesenchymal Transition Reveals Extracellular Clusterin as a Target for Therapeutic Antibodies. Oncogene.

Massague J. TGFbeta in Cancer. (2008) Cell, 134: 215.

Mayer M, Meyer B. (1999) Characterization of ligand binding by saturation transfer difference NMR spectroscopy. Angew Chem, Int Ed. 38:1784-1788.

Mayer M, Meyer B. (2001) Group epitope mapping by saturation transfer difference NMR to identify segments of a ligand in direct contact with a protein receptor. J. Am. Chem. Soc. 123: 6108-6117.

McCormack E, Micklem DR, Pindard LE, Silden E, Gallant P, Belenkov A, Lorens JB, Gjertsen BT. (2007) In vivo optical imaging of acute myeloid leukemia by green fluorescent protein: time-domain autofluorescence decoupling, fluorophore quantification, and localization. Mol. Imaging. 6:193.

Mourra N, Couvelard A, Tiret E, Olschwang S, Flejou JF. (2007) Clusterin is highly expressed in pancreatic endocrine tumours but not in solid pseudopapillary tumours. Histopathology. 50: 331.

Peng L, Liu R, Andrei M, Xiao W, and Lam KS. (2008) In vivo optical imaging of human lymphoma xenograft using a library-derived peptidomimetic against L4i .1 integrin. Mol. Cancer Ther. 7: 432.

Rosenthal EL, Kulbersh BD, King T, Chaudhuri TR, and Zinn KR. (2007) Use of fluorescent labeled anti-epidermal growth factor receptor antibody to image head and neck squamous cell carcinoma xenografts. Mol. Cancer Ther. 6:1230.

Steinberg J, Oyasu R, Lang S et al. (1997) Intracellular levels of SGP-2 (Clusterin) correlate with tumor grade in prostate cancer. Clin. Cancer Res.; 3:1707.

Su Z, Vinogradova A, Koutychonko A, Tolkatchev D, and Ni F. (2004) Rational design and selection of bivalent peptide ligands of thrombin incorporating P4-P1 tetrapeptide sequences: from good substrates to potent inhibitors. Protein Eng. Des. Sel. 17: 647-657.

Wagnieres GA, Star WM and Wilson BC. (1998) In Vivo Fluorescence Spectroscopy and Imaging for Ontological Applications. Photochemistry and Photobiology 68:603.

(Continued)

*Primary Examiner* — Karlheinz R Skowronek
*Assistant Examiner* — Jia-Hai Lee
(74) *Attorney, Agent, or Firm* — Janique Forget

(57) ABSTRACT

Peptides are disclosed that are useful for molecular imaging or diagnosis of a disease state, such as cancer, in which clusterin is upregulated.

19 Claims, 18 Drawing Sheets

(56) References Cited

OTHER PUBLICATIONS

Watari H, Ohta Y, Hassan MK, Xiong Y, Tanaka S, Sakuragi N. (2008). Clusterin expression predicts survival of invasive cervical cancer patients treated with radical hysterectomy and systematic lymphadenectomy. Gynecol. Oncol. 108: 527.

Zhang S, Zhang D, Zhu Y, Guo H, Zhao X, Sun B. (2006) Clusterin expression and univariate analysis of overall survival in human breast cancer. Technol. Cancer Res. Treat. 5:573.

Venter, J. Craig et al.,: Sequence ID No. 33084 from US20050208558A1 "Detection kits, such as nucleic acid arrays, for detecting the expression or 10,000 or more *Drosophila* genes and uses thereof" published on Sep. 22, 2005.

Li Wei et al. (2009) Roles of clusterin in progression, chemoresistance and metastasis of human ovarian cancer, International Journal of Cancer, vol. 125, No. 4, p. 791-806.

Nicolaus B J R (1983) Symbiotic Approach to Drug Design, Decision Making in Drug Research, p. 173-186.

* cited by examiner

```
                         SEQUENCE LISTING


<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Clusterin binding peptide

<400> SEQUENCE: 1

His Pro Leu Ser Lys His Pro Tyr Trp Ser Gln Pro
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Clusterin binding peptide

<400> SEQUENCE: 2

Asn Thr Tyr Trp Ser Gln Leu Leu His Phe Gln Thr
1               5                   10
```

-continued

```
<210> SEQ ID NO 3
<211> LENGTH: 12
<212> TYPE: PRT
<213> ORGANISM: Artificial Sequence
<220> FEATURE:
<223> OTHER INFORMATION: Clusterin binding peptide

<400> SEQUENCE: 3

Ser His Ala Leu Pro Leu Thr Trp Ser Thr Ala Ala
1               5                   10


<210> SEQ ID NO 4
<211> LENGTH: 4
<212> TYPE: PRT
<213> ORGANISM: Artificial Sequence
<220> FEATURE:
<223> OTHER INFORMATION: Portion of clusterin binding sequence

<400> SEQUENCE: 4

Tyr Trp Ser Gln
1


<210> SEQ ID NO 5
<211> LENGTH: 5
<212> TYPE: PRT
<213> ORGANISM: Artificial Sequence
<220> FEATURE:
<223> OTHER INFORMATION: Linker sequence

<400> SEQUENCE: 5

Ser Gly Ser Gly Cys
1               5


<210> SEQ ID NO 6
<211> LENGTH: 17
<212> TYPE: PRT
<213> ORGANISM: Artificial Sequence
<220> FEATURE:
<223> OTHER INFORMATION: Randomized control for P3378

<400> SEQUENCE: 6

Pro Tyr Leu His Gln Ser Pro His Trp Lys Pro Ser Ser Gly Ser Gly
1               5                   10                  15

Cys


<210> SEQ ID NO 7
<211> LENGTH: 17
<212> TYPE: PRT
<213> ORGANISM: Artificial Sequence
<220> FEATURE:
<223> OTHER INFORMATION: Randomized control for P3375

<400> SEQUENCE: 7

Leu Ser Leu Tyr His Thr Asn Thr Gln Phe Trp Gln Ser Gly Ser Gly
1               5                   10                  15

Cys


<210> SEQ ID NO 8
<211> LENGTH: 17
<212> TYPE: PRT
<213> ORGANISM: Artificial Sequence
<220> FEATURE:
<223> OTHER INFORMATION: Randomized control for P3376

<400> SEQUENCE: 8

Ala Trp His Thr Leu Ala Ser Thr Ser Leu Ala Pro Ser Gly Ser Gly
```

-continued

```
1               5                   10                  15

Cys
```

PEPTIDE LIGANDS FOR CLUSTERIN AND USES THEREOF

CROSS-REFERENCE TO RELATED APPLICATIONS

This application is a national entry of International Patent Application PCT/CA2010/000566 filed Apr. 15, 2010 and claims the benefit of United States Provisional Patent Application U.S. Ser. No. 61/202,910 filed Apr. 17, 2009, the entire contents of both of which are herein incorporated by reference.

FIELD OF THE INVENTION

The present invention relates to peptide ligands specific for clusterin and uses thereof. More specifically, the present invention relates to clusterin-binding peptides and their use in molecular imaging.

BACKGROUND OF THE INVENTION

The use of molecular imaging in basic research, while not a new technique, has shown important growth with the advent of molecular biology techniques and the outcome of various genome sequencing projects. This technology may have a significant impact on clinical care in the future, as it has the potential for applications in the diagnosis of diseases such as neurological diseases, cardiovascular diseases and cancer.

The development of probes, or molecular imaging agents, that specifically seek out targets in living organisms is one of the key fundamentals in this area of research. Genomics and proteomics research has already uncovered many new potential targets. Imaging agents against these new targets will not only help understand their roles in disease progression, but will also aid in the generation and assessment of new therapeutics. The probes generally comprise a targeting moiety, which allows the probe to home in on the target molecule, and an imaging moiety, which allows for detection of the probe.

Ideally, a molecular imaging agent should have appropriate affinity, specificity, and metabolic stability, such that it homes in on its target with sufficient concentration and retention time in order to be detectable in vivo. Ideally, it should also have a relatively short half-life in the circulation, and display very low non-specific binding. Many types of imaging moieties have been used in molecular imaging; for example, radiolabels, fluorophores, and Near Infra-Red (NIR) fluorochromes. Targeting moieties have included monoclonal antibodies, lipoproteins, and polypeptides. These and other types of targeting moieties have been utilized to generate optical probes, which have been used by many investigators for the optical imaging of different types of tumors (Wagnières et al., 1998; Rosenthal et al., 2007; McCormack et al., 2007; Peng et al., 2008). One advantage of NIR probes is their capacity for imaging of deeper tissues due to their properties of high penetration, low tissue absorption and scattering.

In post-genomics biotechnology and drug discovery research, there is a great interest in developing peptide-based molecules that home to new targets as the next generation of more versatile targeting moieties. Peptide-based targeting moieties typically show lower affinity for their target than monoclonal antibodies. However, whereas antibodies have limitations that are linked to poor diffusion and target accessibility, peptides have advantages such as small size (which implies good tissue penetration), easy synthesis and a faster clearance rate from the circulation (which can lead to good contrast). To date, the identification of effective peptide-based targeting moieties has been focused primarily on peptides that interact with vascular targets.

Of particular interest within the molecular imaging field is its potential as a tool for diagnosing cancers and assessing response to treatment. Carcinomas are the most common human malignancy, and arise from epithelial cells. Progression of epithelial cancers begins with the disruption of cell-cell contacts as well as the acquisition of a migratory (mesenchymal-like) phenotype. This phenomenon, which is called an epithelial-to-mesenchymal transition (EMT), is considered to be a crucial event in late stage tumor progression and metastasis (Gupta and Massague, 2006; Berx et al., 2007). One of the key players in EMT is the secreted protein TGF-β, which suppresses tumor growth initially largely due to its growth inhibitory action on tumor cells of epithelial origin, then at later stages promotes tumor cell progression and metastasis (Massague, 2008). One mechanism by which TGF-β can promote tumor progression is through the induction of an EMT.

The development of improved imaging probes that target the molecular mechanisms associated with tumor formation and progression would be beneficial in the diagnosis and ongoing assessment of cancer, and possibly in the development and assessment of therapeutics.

SUMMARY OF THE INVENTION

The present invention relates to peptide ligands specific for clusterin and uses thereof. More specifically, the present invention relates to clusterin-binding peptides and their use in molecular imaging.

The present invention is directed to peptides comprising:

```
                         (SEQ ID NO: 1)
a) the sequence HPLSKHPYWSQP;

                         (SEQ ID NO: 2)
b) the sequence NTYWSQLLHFQT;
and

                         (SEQ ID NO: 3)
c) the sequence SHALPLTWSTAA,
```

or a sequence substantially identical thereto.

The present invention also provides a peptide as described above linked to a cargo molecule.

The peptides as described above may be used for molecular imaging, or in the diagnosis or treatment of disease states in which clusterin is upregulated, such as cancer.

The novel clusterin-binding peptides of the present invention have been shown to interact specifically with clusterin, and to selectively home to solid tumors. Because of their favourable binding specificities, affinities, and clearance rates from the circulation, these peptides may be used as tools for molecular imaging. Peptide-based molecules of this type could therefore represent the next generation of more versatile targeting agents.

In one aspect, the present invention also provides a method of imaging a tumor comprising linking a peptide as described above to a cargo molecule comprising an imaging moiety, administering the peptide linked to the cargo molecule to a subject, and detecting the imaging moiety in the subject.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIGS. 3A and 3B are expansions of the NMR-STD spectra shown in FIG. 2 (bottom panel) and FIG. 3C.

FIG. 10A), P3375 (P3375R; FIG. 10B) and P3376 (P3376R; FIG. 10C) sequences.

FIG. 11A illustrates the binding of clusterin to immobilized P3378, while FIG. 11B shows the binding of mixtures of clusterin: 16B5 to immobilized P3378.

FIG. 16A depicts morpholgy of the 4T1 cells when cultured in 2D (magnification: 40×). FIG. 16B depicts Western blot of the whole cell lysate (WCL) and conditioned medium (CM) shows the presence of unprocessed (pCLU) and processed secreted (sCLU) clusterin in the WCL, whereas processed-secreted sCLU can only be found in the CM. FIG. 16C depicts immunofluorescent microscopy showing the presence of secreted CLU in isolated 4T1 tumors compared to DAPI-stained nuclei (magnification 10×).

FIG. 18 shows that accumulation of P3378-DL680 can be blocked by excess unlabeled P3378 but not P3378R.

DETAILED DESCRIPTION OF THE INVENTION

Figure 1:
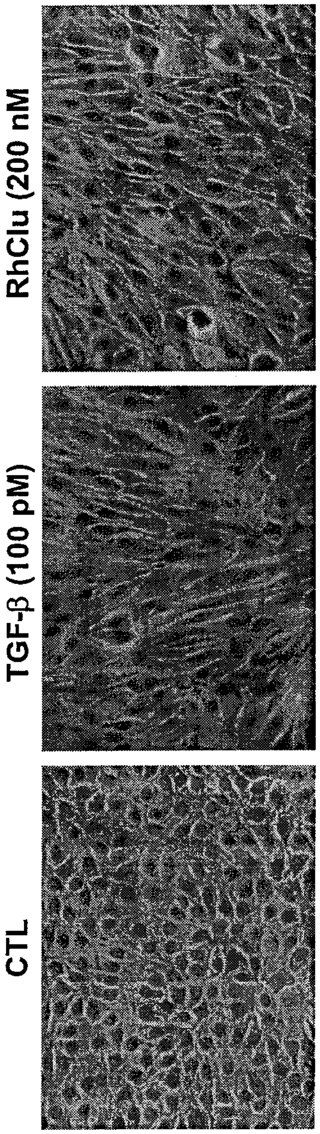
FIG. 1 shows that TGF-β and recombinant human clusterin (rhCLU) induce the Epithelial-to-Mesenchymal Transition (EMT). EMT is characterized by the elongation (among other features) of the cells.

The present invention relates to peptide ligands specific for clusterin and uses thereof. More specifically, the present invention relates to clusterin-binding peptides and their use in molecular imaging.

It has been shown that clusterin mRNA is up-regulated when BRI-JM01 mouse mammary cells are exposed to Transforming Growth Factor (TGF)-β, which results in the secretion of clusterin (O'Connor-McCourt et al, WO 2007/030930). Clusterin has been further implicated as playing a pivotal role in the TGF-β-induced EMT of BRI-JM01 cells (Lenferink et al., submitted), and the epitope within clusterin that is responsible for its EMT-promoting action has been identified (O'Connor-McCourt et al, WO 2007/030930). Other reports have shown clusterin as playing additional important functions that promote tumorigenesis, e.g. antiapoptotic activities (Lau et al., 2006; Mourra et al., 2007; Zhang et al., 2006; Watari et al., 2008, and Steinberg et al., 1997).

The present invention is directed to peptides that bind specifically to clusterin glycoprotein. Specifically, the present invention is directed to peptides comprising:

```
                                (SEQ ID NO: 1)
a) the sequence HPLSKHPYWSQP,
referred to herein as P3378;

                                (SEQ ID NO: 2)
b) the sequence NTYWSQLLHFQT,
referred to herein as P3375;
and

                                (SEQ ID NO: 3)
c) the sequence SHALPLTWSTAA,
referred to herein as P3376.
```

The present invention also encompasses peptides with a sequence substantially similar to the sequences of peptides P3378, P3375, and P3376. A substantially identical peptide may comprise one or more conservative amino acid mutations. It is known in the art that one or more conservative amino acid mutations to a reference peptide may yield a mutant peptide with no substantial change in physiological, chemical, or functional properties compared to the reference peptide; in such a case, the reference and mutant peptides would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as BLAST-P, BLAST-N, or FASTA-N, or any other appropriate software that is known in the art. The substantially identical sequences of the present invention may be at least 75% identical. In another example, the substantially identical sequences may be at least 75, 80, 85, 90, 95, or 100% identical at the amino acid level to sequences described herein.

The P3378, P3375, and P3376 peptides of the present invention were obtained by screening a phage-displayed peptide library against full-length recombinant human clusterin. Nuclear Magnetic Resonance (NMR) spectroscopy and Surface Plasmon Resonance (SPR) biosensor studies confirmed that the peptides bind clusterin in a specific manner.

The present invention also encompasses the clusterin-specific peptides as described herein linked to a cargo molecule. The cargo molecule may be any suitable molecule known in the art, and may be useful in the diagnosis or treatment of carcinoma or other disease states in which clusterin is upregulated. For example, and without wishing to be limiting, the cargo molecule may be an enzyme, an imaging moiety used in molecular imaging, a radioisotope useful in identification and localization of cells of interest in tissue, or a cytotoxic agent such as a drug, antigen, apoptosis inducer or radioisotope useful in reducing the viability of diseased tissue or the ability of a carcinoma cell to proliferate.

In one embodiment, the cargo molecule may be an imaging moiety. The molecular imaging moiety may be any suitable molecule. In a non-limiting example, the imaging moiety may be a radiolabel, fluorophore, Near Infra-Red (NIR) fluorochrome or magnetic nanoparticle. In a further, non-limiting example, the imaging moiety may be Alexa680, Dylight680, or Dylight800, Cy5.5 dye, or any other fluorophore known in the art.

The cargo molecule may be linked to the peptide by any method know in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. Methods for linking the peptides of the present invention to a cargo molecule would be well known to a person of skill in the art.

The peptides as described above may be used in several molecular imaging technologies, including:

Optical imaging, as described herein;

Positron emission tomography (PET) by labeling the peptides with typical isotopes such as $^{11}$C, $^{13}$N, $^{15}$O, $^{18}$F, $^{64}$Cu, $^{62}$Cu, 1$^{24}$I, $^{76}$Br, $^{82}$Rb and $^{6}$8Ga, with $^{18}$F being the most clinically utilized;

Single photon emission computed tomography (SPECT) using radiotracers such as $^{99m}$Tc, $^{111}$In, 123I, $^{201}$Tl, depending on the specific application. For example, and without wishing to be limiting, $^{133}$Xe gas has been shown to be valuable for diagnostic inhalation studies for the evaluation of pulmonary function;

Magnetic resonance imaging (MRI) by coupling the peptides to, for example and not limited to carbon-coated iron-cobalt nanoparticles thereby increasing the sensitivity of MRI for the detection of tumors. This type of nanoparticle can also absorb near-infrared light and generate heat, which not only allows for the imaging of tumors, but may also enable heat killing of tumor cells.

The optimal dose of injection and method of administration (intravenous (i.v.) or intraperitoneal (i.p)) are generally determined experimentally.

Figure 12:
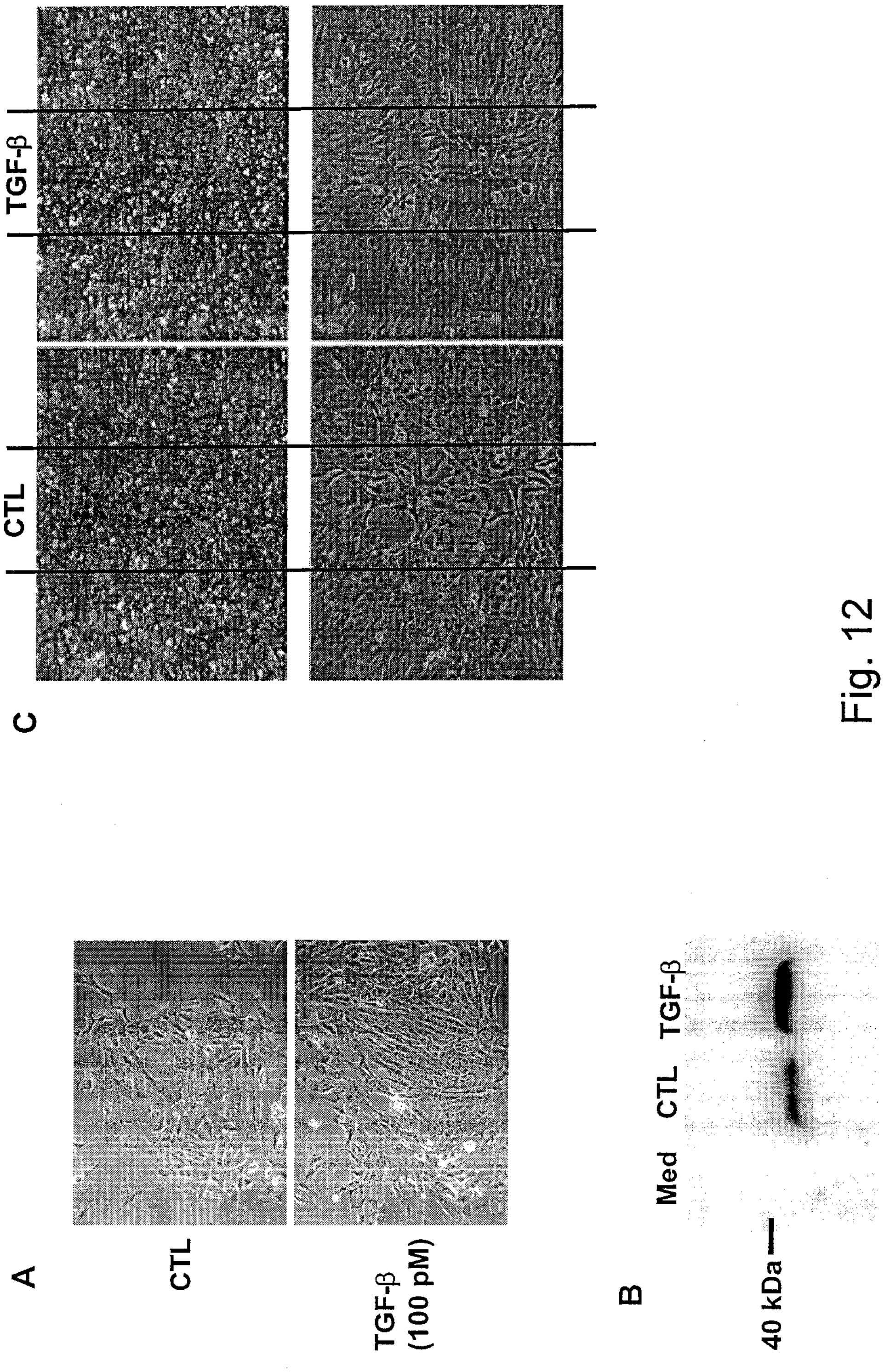
FIG. 12A shows that 4T1 mouse mammary tumor cells undergo a very subtle mesenchymal-like morphology change when grown in the presence of TGF-β for 24 hrs, compared to the non-treated cells (CTL).
FIG. 12B is a Western blot analysis of the amount of clusterin in conditioned medium obtained from cells that were grown in the absence (CTL) or presence of TGF-β for 24 hrs. The medium control is labeled "Med".
FIG. 12C illustrates that the endogenous motility of 4T1 cells is increased by the presence of TGF-β, as shown in a wound healing assay. Top panels show cell monolayers at low magnification; bottom panels at higher magnification; lines indicate the original width of the wound.
Figure 13:
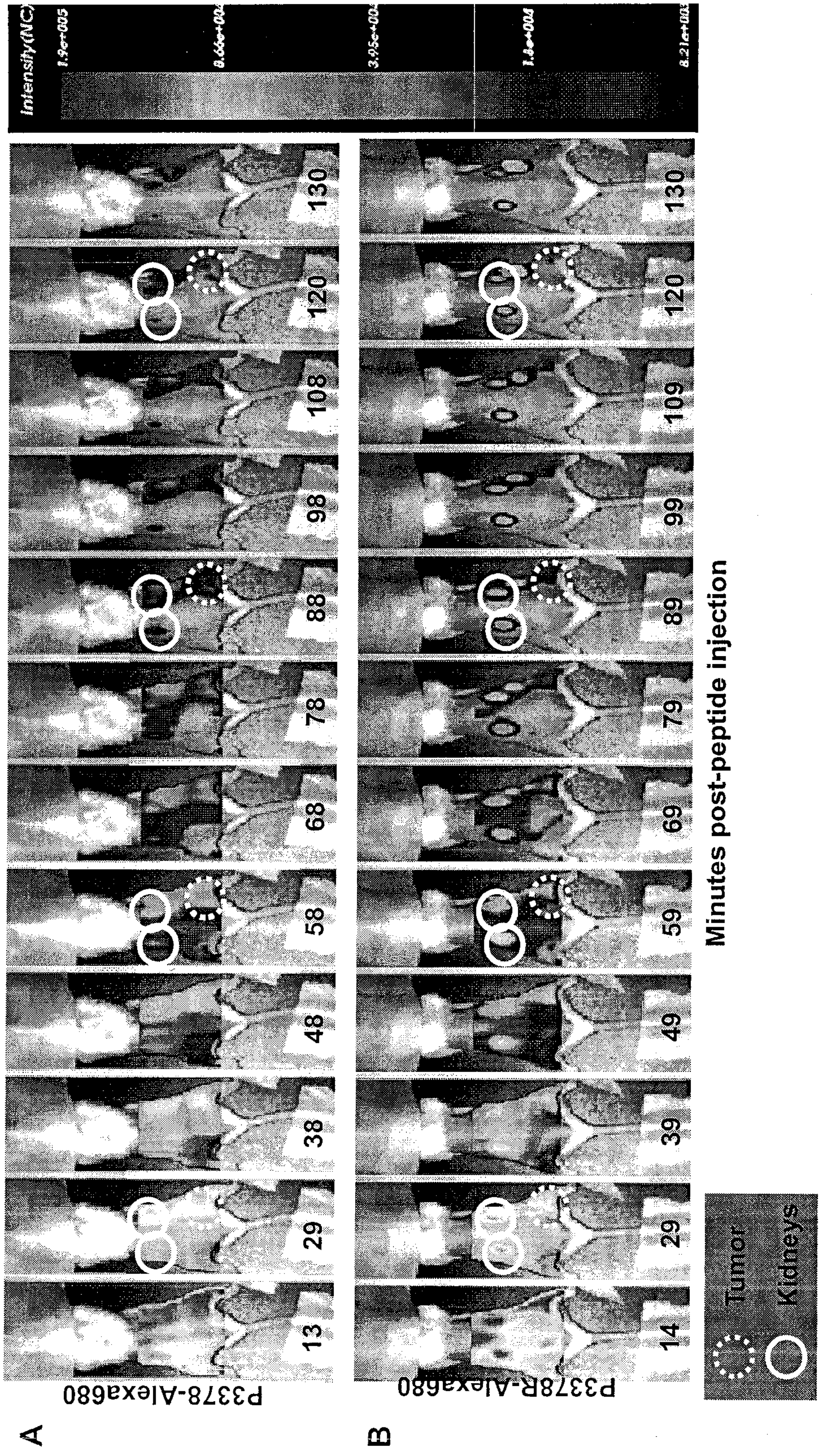
FIG. 13 shows representative images of time dependant fluorescence intensity maps following the distribution in 4T1 tumor bearing mice of the clusterin binding peptide P3378 (FIG. 13A), and the scrambled control peptide P3378R (FIG. 13B), both labeled with the Alexa680 fluorophor, from 14 to 130 min post-peptide injection. Dashed line circles indicate P3378-Alexa680 peptide at the tumor site, while solid line circles show the P3378R peptide in the kidneys.

The peptides as described herein may be used for the diagnosis, assessment of treatment, or treatment of cancers and other disease conditions in which clusterin is overexpressed. As clusterin has been implicated in EMT of carcinomas (FIG. 1), the present clusterin-binding peptides may be used to detect the progression of carcinomas by molecular imaging techniques. In fact, real-time imaging on live mice demonstrated the ability of the P3378 peptide to home to and image tumors in vivo when fluorescently labeled with Near Infra Red (NIR) probes (FIGS. 12 and 13). This may allow the localization, visualization and quantification of tumors in vivo, as well as providing information regarding optimal biopsy sites and tumor margins for resection.

The novel clusterin-binding peptides of the present invention have been shown to bind specifically to clusterin, and to selectively home to solid tumors. Their binding specificity, lower binding affinity (as compared to monoclonal antibodies), and faster clearance rate from the circulation (as compared to monoclonal antibodies), has enabled these peptides to act as useful tools for molecular imaging, as they provide good contrast in imaging studies.

The present invention will be further illustrated in the following examples. However, it is to be understood that these examples are for illustrative purposes only and should not be used to limit the scope of the present invention in any manner.

Example 1

Identification of Clusterin-Binding Peptides Through Phage Display

Peptides that bind to human clusterin were identified through phage-display technology.

Purified recombinant human clusterin (rh-clusterin) preparations used for phage panning, SPR, NMR, were produced in HEK-293 cells (general expression system described in Durocher et al, 2002).

The commercially available Ph.D.-12 phage display library kit, displaying random 12-amino acid peptides, was purchased from New England BioLabs (Beverly, Mass.). MaxiSorp™ wells (Nunc Brand, Denmark) were coated with 10 μg rh-clusterin in 100 μL PBS, pH 7.4, overnight, at 4° C., and blocked with 0.5% BSA for 1 hour.

Panning procedure was performed at room temperature essentially as described elsewhere (Su et al, 2004). After each panning round 20 phage clones were randomly picked and sequenced.

Two panning rounds of the phage library against purified rh-clusterin led to considerable enrichment (up to 35% of analyzed plaques) of a single phage clone containing a unique peptide with amino acid sequence HPLSKHPYWSQP (SEQ ID NO:1), designated P3378.

The third panning round returned almost exclusively phage particles displaying P3378. Thus, identifying another peptide sequence family with affinity for rh-clusterin was difficult. To identify other peptide ligands interacting with rh-clusterin, a PhD-12 phage sublibrary obtained after the first selection round was subjected to two successive panning cycles in the presence of competing P3378 (1 mM). These rounds yielded more peptide sequences with possible binding to rh-clusterin. On the basis of occurrence frequency, two additional sequences were chosen for further analysis: NTYWSQLLHFQT (P3375) (SEQ ID NO: 2) and SHALPLTWSTAA (P3376) (SEQ ID NO: 3). It is worth noting that both P3375 and P3378 contain the sequence YWSQ (SEQ ID NO:4).

Example 2

Synthesis of Peptides P3375, 3376, and 3378

The three peptide sequences identified in Example 1 were synthesized using standard Fmoc chemistry with an extension at the COOH terminus, i.e. they were extended by a SGSGC sequence (SEQ ID NO:5) to provide a linker for coupling to the SPR biosensor surface, or to NIR dyes, through stable thioether bonds Unlabeled synthetic peptides were synthesized using standard Fmoc chemistry. Peptides were purified by use of HPLC on a Vydac™-C18 reversed-phase column, 10×250 mm, using a water-acetonitrile linear gradient of 0-60% (1.0%/min, flow rate 5.0 ml/min) with added 0.1% trifluoroacetic acid (TFA). Final products were lyophilized; a purity of ≥98% for all peptides was confirmed by analytical HPLC on a Vydac-C18 reversed-phase column, 4.6×250 mm, using the gradient of 0-60% (1%/min, flow rate 1.0 ml/min) acetonitrile in 0.1% TFA. The elution profile was monitored by absorbance at 278 nm. The identities of all purified peptides were verified by electrospray mass spectrometry (ESI-MS). Peptide concentrations were determined spectrophotometrically using predicted extinction coefficients.

Example 3

Characterization of the Interactions of Peptides with Clusterin using STD-NMR To confirm direct binding of the peptides of Example 1 to clusterin, the interaction of the synthetic peptides of Example 2 with clusterin was tested using Nuclear Magnetic Resonance Saturation Transfer Difference (STD-NMR; Mayer & Meyer, 2001)

NMR samples were prepared by dissolving 0.15 mM of peptides in 50 mM sodium phosphate buffer, 0.2 mM EDTA, pH 6.5. rh-clusterin (~1 mg/ml) in 5 mM sodium phosphate buffer, 0.02 mM EDTA, pH 7.4, was added to ~1:30 protein:peptide ratio.

All NMR experiments were performed at 298K on a Bruker Avance800™ NMR spectrometer equipped with a 5 mm triple-resonance probe with three-axis gradients. Saturation transfer difference (STD) spectra was recorded using WATERGATE version of STD pulse sequence (35) with a 3 s selective saturation pulse applied in the relaxation delay and a 20 ms spinlock pulse with a field strength of 12.25 kHz. The saturation pulse was implemented using a pulse train of 49 ms Gaussian-shaped selective pulse and 1 ms interpulse delay. Each Gaussian-shaped pulse had 1000 points with a 1% truncation and was applied with a field strength of 75.9 Hz. STD spectra were recorded with a spectral width of 16025.64 Hz and 32 K data points. Time domain signals were accumulated with 1024 and 4096 scans for the free and complexed sample, respectively. NMR data were processed using Bruker Xwinnmr 2.6. An exponential weighting function of 7 Hz was applied prior to Fourier transformation and polynomial baseline correction.

NMR signals of peptide P3378 and rh-clusterin were severely overlapped, making it impossible to apply the above saturation pulse exclusively on rh-clusterin resonances without disturbing those of the peptide. In order to identify the binding interactions in the P3378-rh-clusterin complex, a new experimental scheme was implemented by applying the on-resonance saturation pulse at methyl resonances (0.912 ppm) and the off-resonance irradiation at −7.799 ppm (referenced $H_2O$ to 4.700 ppm). In this scheme, the on-resonance saturation pulse quenched the NMR signals around the methyl resonances while the off-resonance irradiation had no effect on the whole NMR spectrum, as it was applied to a spectral region without any resonances. A STD spectrum was obtained by subtracting the on-resonance irradiated spectrum from the off-resonance irradiated spectrum. As a result of differential spectrum, strong "residual" peaks around the frequency of on-resonance were observed in the STD spectra of the complex, even though there was no binding interaction between the peptide and protein. The on-resonance irradiation at methyl frequency saturates not only the protein signals but also the peptide signals close to the on-resonance. This may lead to additional STD signals that are from the intra-peptide saturation transfer effect. In order to evaluate this intra-peptide effect, the same experimental setup was also performed for the free peptide sample. The binding information can be extracted by comparing the STD spectrum of the complex with that of the free peptide.

Figure 2:
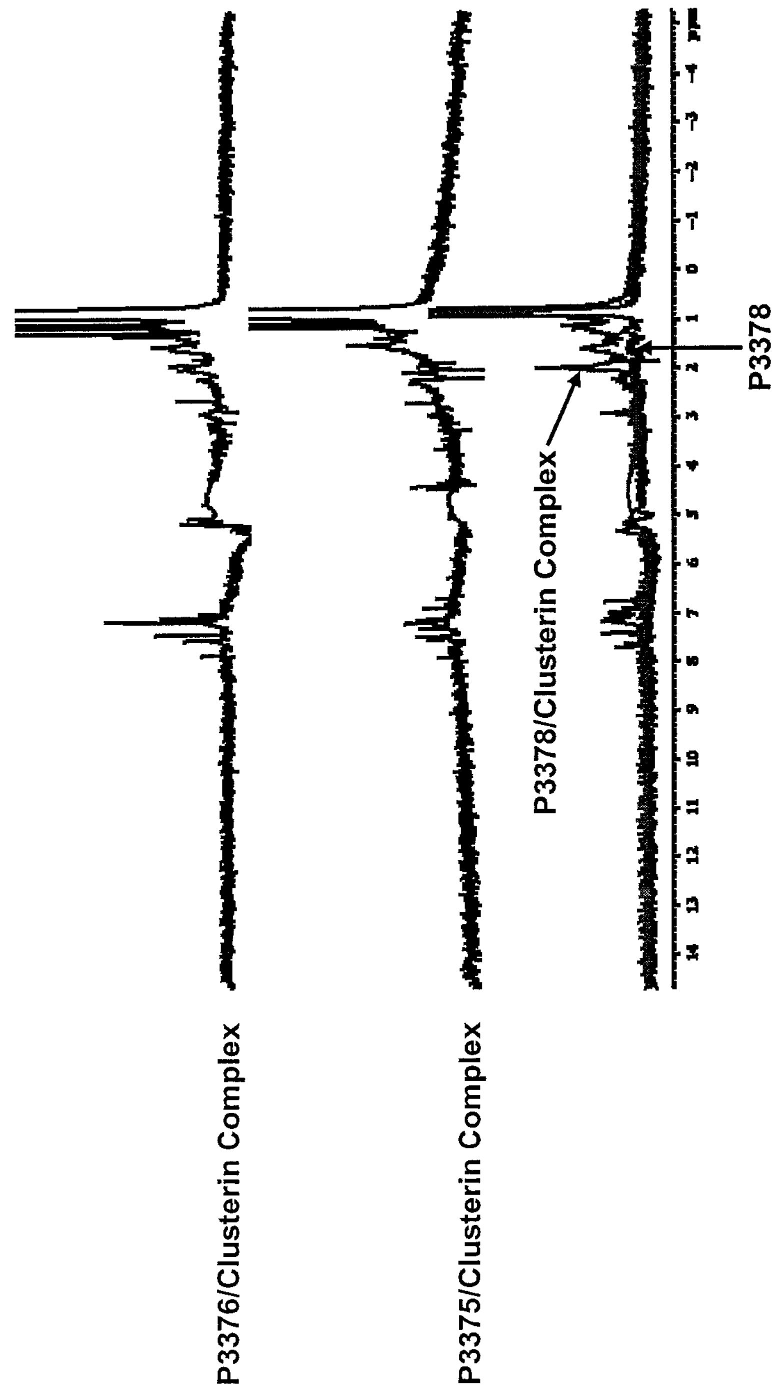
FIG. 2 shows Nuclear Magnetic Resonance Saturation Transfer Difference (NMR-STD) spectra demonstrating binding of identified peptides to clusterin. The top panel is the P3376/clusterin complex; the middle panel is the P3375/clusterin complex; and the bottom panel is the overlay of the P3378/clusterin complex and P3378 alone. The difference between the STD spectra in the absence (solid arrow) and presence (dashed arrow) of clusterin demonstrates binding.
Figure 3:
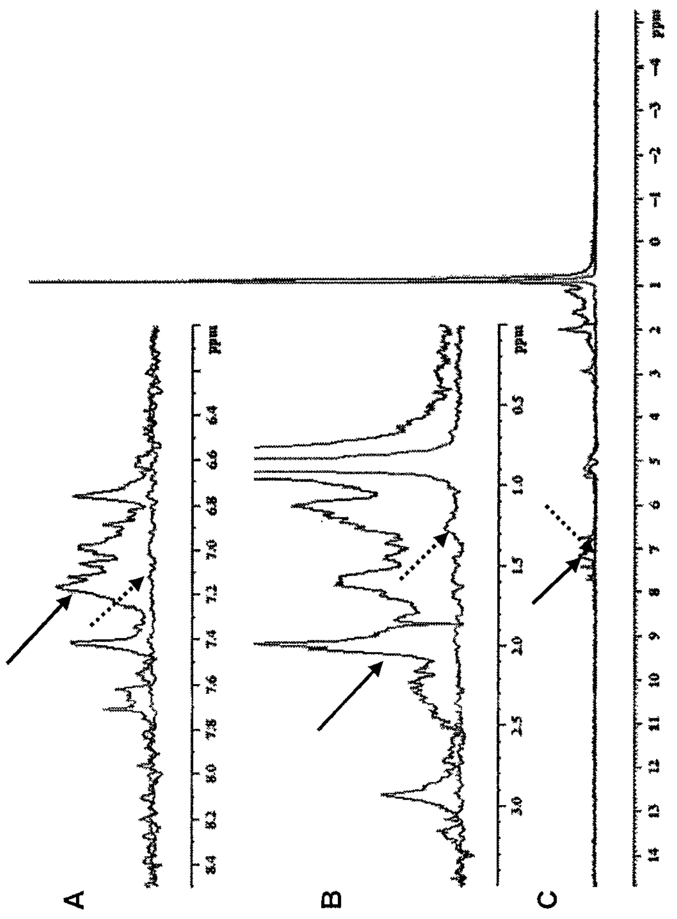
FIGS. 3A-C show NMR-STD spectra of the P3378-Clusterin complex (solid arrows) and P3378 alone (dashed arrows) illustrating binding of peptide (P3378) to rhCLU.

FIG. 2 (bottom panel) shows STD-NMR spectra of P3378 in the presence and absence of substoichiometric amounts of clusterin (~1:30 protein:peptide). The appearance of sharp NMR peaks in the aromatic side chain region (~7 ppm) in the presence of rh-clusterin implied transfer of saturation from protein to peptide and indicated direct interaction between them. Similarly to P3378, binding of synthetic P3375 and P3376 was confirmed by STD-NMR (FIG. 2, top and middle panels). The NMR-STD spectra of the P3378-clusterin complex (solid arrows) and P3378 alone (dashed arrows) demonstrating specific binding of P3378 to rhCLU are illustrated again in FIGS. 3A-C.

Example 4

Characterization of the Interactions of Peptides with Clusterin Using SPR Biosensor Analysis Binding of the peptides of Example 1 to clusterin was further investigated using Surface Plasmon Resonance (SPR).

Peptides were immobilized on research-grade CM5 sensor chips by a maleimide coupling method. CM5 sensor chips (research grade) and EDC were purchased from Biosensor AB (Uppsala, Sweden). This thiol coupling generates a stable thioether bond between reactive maleimide groups on the sensor chip surface and the thiol groups of the peptides. A heterobifunctional reagent, SMCC-hydrazide (4-[N-maleimidomethyl]cyclohexane-1 carboxylhydrazide; 99.5% pure; purchased from Molecular Biosciences Inc. (Boulder, Colo.)), was used to introduce reactive maleimido groups to the sensor surface. Immobilization was performed at 25° C. at a flow rate of 5 μL/min. A continuous flow of the HBS-EP buffer (20 mM HEPES, 150 mM NaCl, 3.4 mM EDTA and 0.05% Tween™-20 at pH 7.4) was maintained over the sensor surface. The carboxylated dextran matrix on the sensor surface was activated by an injection of 50 μL of a freshly mixed solution containing 172 μL of 1.2 mM N-ethyl-N'-(3-diethylaminopropyl)carbodiimide (EDC) in 100 mM MES buffer at pH 5.00, and 28 μL of 17.8 mM SMCC-hydrazide in 40% DMF. The ratio of the SMCC:EDC was 2.5:1. Peptide-coupled surfaces were generated by injecting peptides (30-100 μg/ml) in 100 mM MES buffer (at pH 5.0). The amount of peptide immobilized on the activated surface was controlled by altering the contact time with the peptide solution and was between approximately 400 and 500 RU, or 400-500 pg peptide/$mm^2$. The immobilization procedure was completed by a 50 μL injection of 50 mM cysteine in 1 M sodium chloride and 0.1M sodium acetate (pH 4) to quench excess active maleimide groups.

Protein-peptide interactions were followed using a BIAcore 3000 instrument (Biosensor AB, Uppsala, Sweden). All binding experiments were carried out at 25° C. under a continuous flow of the HBS-EP buffer (20 mM HEPES, 150 mM NaCl, 3.4 mM EDTA and 0.05% Tween-200) at pH 7.4 over the sensor surface at a flow rate of 20 μL/min. Different concentrations of rh-clusterin in the HBS-EP buffer were injected over the peptide-derivatized sensor chips. Dissociation was monitored for up to 300 s post-injection. The surfaces were fully regenerated by 15 s injection of an HBS-EP buffer solution containing 5 mM NaOH. The kinetics of each interaction was negligibly affected by alternating the flow rate (20-100 μL/min), indicating that mass transport contributions were minimal (data not shown). Reference responses from control flow cells, containing unmodified dextran surfaces, were subtracted from peptide-containing flow cells, for each analyte injection using the BiaEvaluation software version 3.0 (Biacore AB, Uppsala, Sweden).

The resulting sensorgrams were used for kinetic rate determination through global fitting of the experimental data to a simple 1:1 Langmuir binding model. Statistical analysis of the fits for both dissociation and association phases of the sensorgrams showed low $_{\chi}2$ values (<2). Affinity data ($K_D$) from the binding studies were obtained by plotting the response in RU at the steady state, Req, versus the concentration of clusterin, C, and by fitting these curves to a one-site binding model, Req=C*xRmax/(C+KD) where Rmax is the value in RU at saturation and Req is the observed optical change in RU at each given C.

Figure 4:
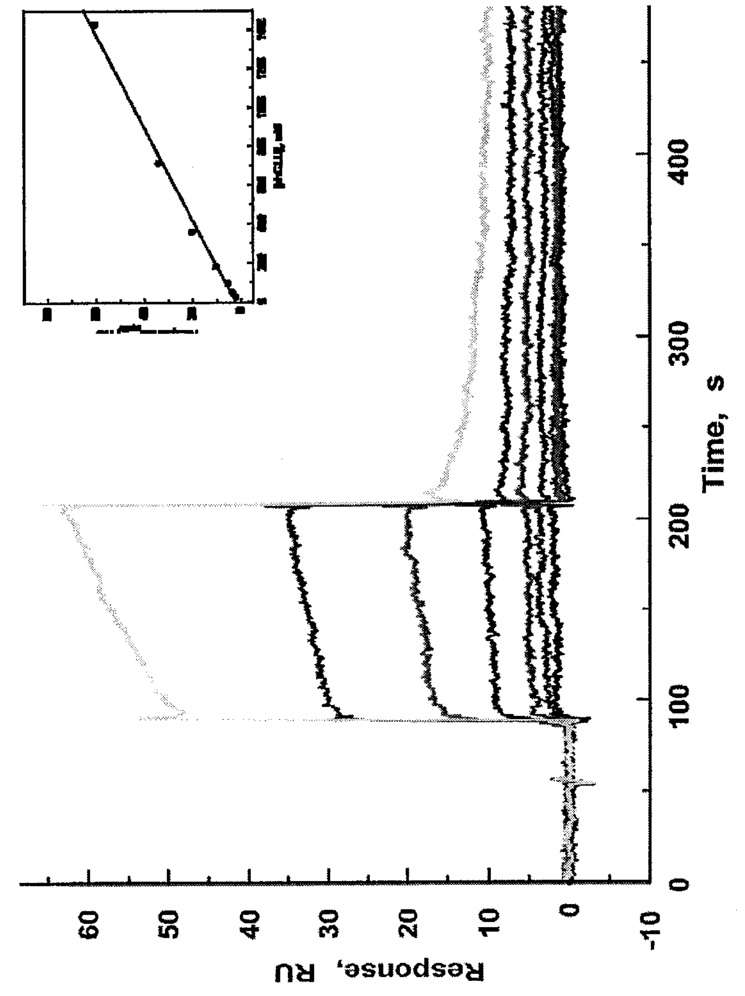
FIG. 4 is an overlay plot of SPR biosensor sensorgrams illustrating that a control peptide (P3378R) does not bind to rhCLU. The Scatchard plot is shown in the inset.

FIG. 4 is an overlay plot of SPR biosensor sensorgrams from a control experiment in which the interaction of rhCLU (11 nM-14 μM) with immobilized randomized sequence P3378R (3378 RUs) was assessed. This control peptide has the same amino acid content as P3378 but with a randomized sequence (PYLHQSPHWKPSSGSGC—SEQ ID NO:6). A lack of binding between rhCLU and this control peptide is evidenced by the linear nature of the Scatchard plot (inset; the response at equilibrium plotted against the concentration of rhCLU). This demonstrates that the randomized peptide does not bind to rhCLU specifically, and consequently that the interaction of the parent P3378 peptide with clusterin is peptide sequence-dependent.

Figure 5:
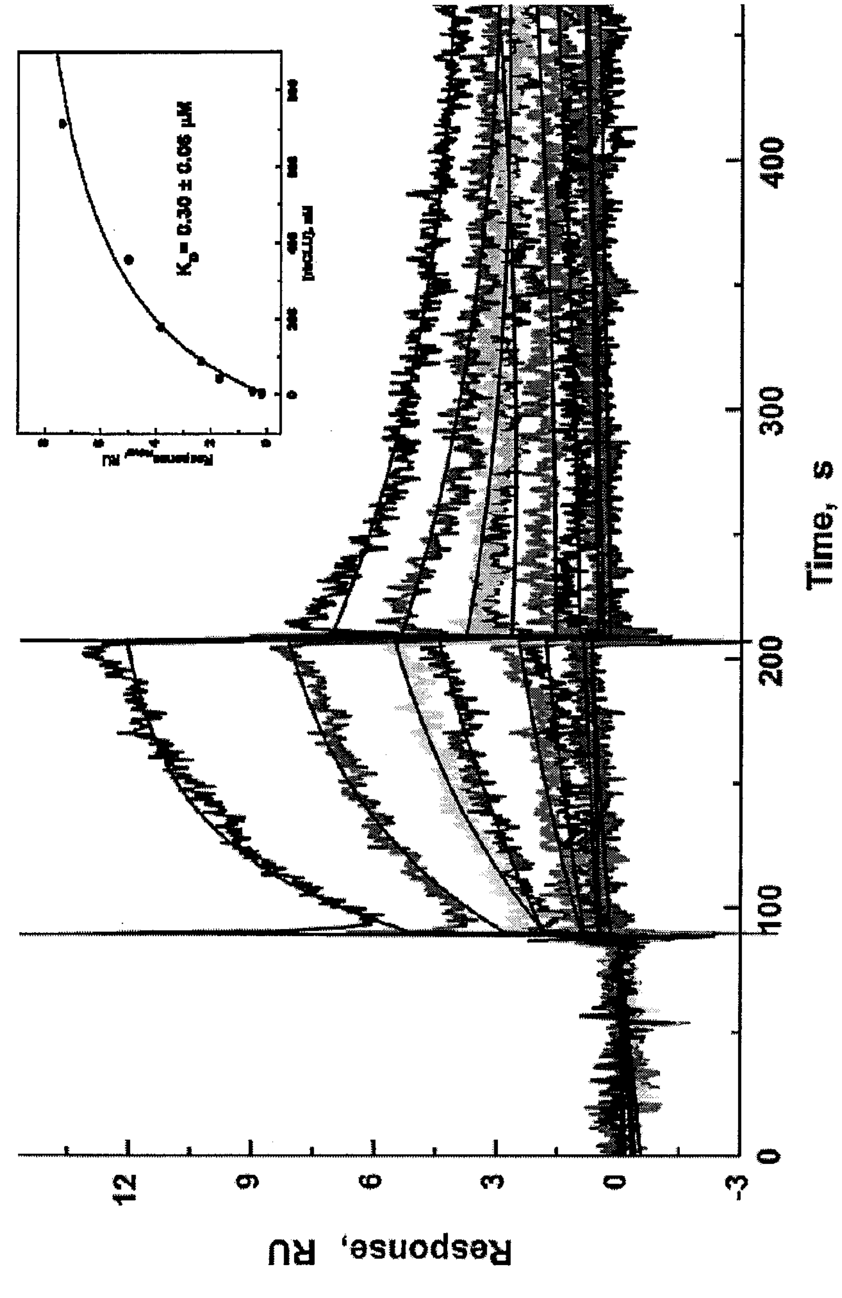
FIG. 5 is an overlay plot of SPR biosensor sensorgrams showing the binding of rhCLU to immobilized peptide P3378. The Scatchard plot is shown in the inset.

FIG. 5 shows an overlay plot of SPR biosensor sensorgrams illustrating the binding of rhCLU (5.5 nM-1.4 μM) to immobilized peptide P3378 (500 RU). A global fit of the data (solid lines) shows that the binding can be described by a simple one-to-one Langmuir binding model with $k_{on}$=(1.72±0.03)x$10^4$ $M^{-1}s^{-1}$, $k_{off}$=0.0052±0.0002 $s^{-1}$ and $K_d$=0.30 μM. The response at equilibrium is plotted against the concentration of rhCLU, and the experimental data were fitted with a one-to-one binding model with Kd of 0.30±0.06 μM. Binding is evidenced by the curvilinear nature of the Scatchard plot (inset).

Figure 6:
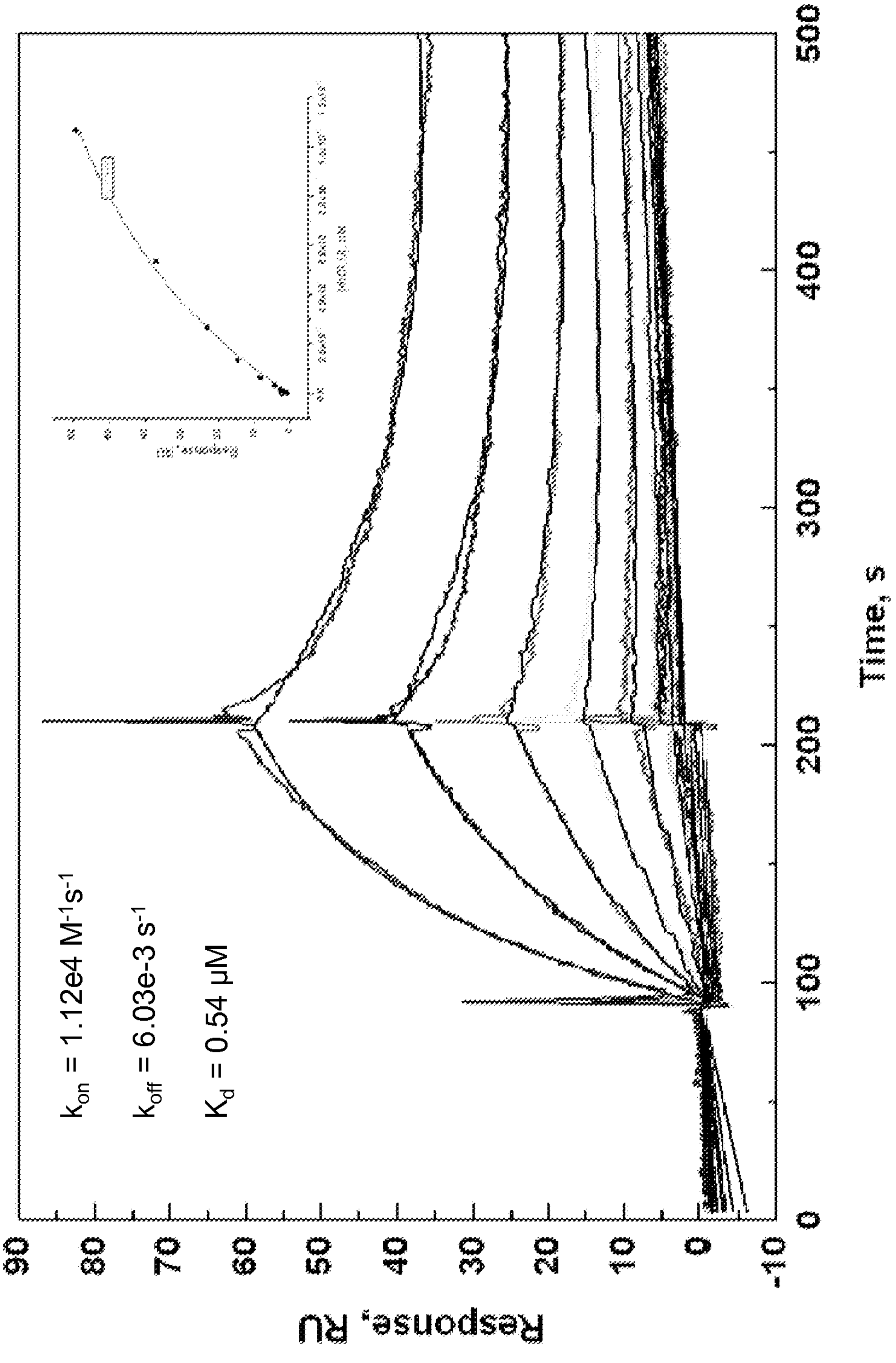
FIG. 6 is an overlay plot of SPR biosensor sensorgrams showing the binding of rhCLU to immobilized peptide P3375. The Scatchard plot is shown in the inset.

FIG. 6 shows an overlay plot of SPR biosensor sensorgrams illustrating the binding of rhCLU (2 nM-1.1 μM) to immobilized peptide P3375 (1200 RU). A global fit of the data (solid lines) shows that the binding can be described by a simple one-to-one Langmuir binding model with $k_{on}$=(1.12±0.03)x$10^4$ $M^{-1}s^{-1}$, $k_{off}$=0.006±0.0002 $s^{-1}$ and $K_d$=0.54 μM. Binding is evidenced by the curvilinear nature of the Scatchard plot (inset).

Figure 7:
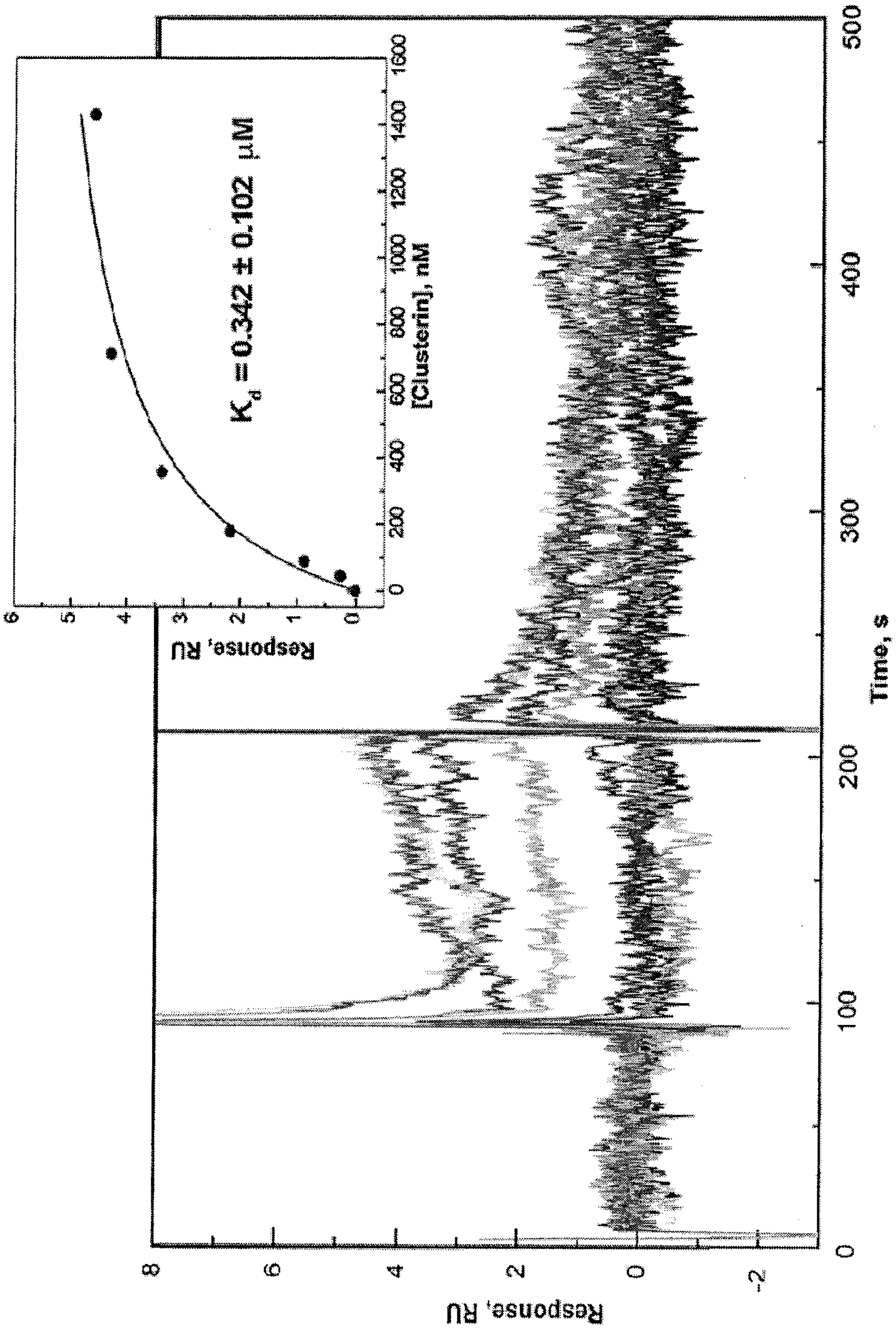
FIG. 7 is an overlay plot of SPR biosensor sensorgrams showing the binding of rhCLU to immobilized peptide P3376. The Scatchard plot is shown in the inset.

FIG. 7 shows an overlay plot of SPR biosensor sensorgrams illustrating the binding of rhCLU (0 nM to 1.4 μM) to immobilized peptide P3376 (150 RU). The response at equilibrium is plotted against the concentration of rhCLU; the curve represents the fit of data points to a one-to-one binding model with $K_d$ of 0.34±0.10 μM. Binding is evidenced by the curvilinear nature of the Scatchard plot (inset).

In summary, FIGS. 5, 6 and 7 demonstrate that all three clusterin-binding peptides that were identified through phage display screening exhibit apparent submicromolar affinities for rh-clusterin.

Example 5

Characterization of the Investigation of the Specificity of the Clusterin-Peptide Interactions Using SPR Biosensor Analysis and Proteins Unrelated to Clusterin The specificity of the clusterin-peptide interactions was investigated using SPR biosensor analysis and proteins unrelated to clusterin. Immobilization of the peptides and other proteins on the sensor chips and the SPR experiments were conducted as described in Example 4.

Figure 8:
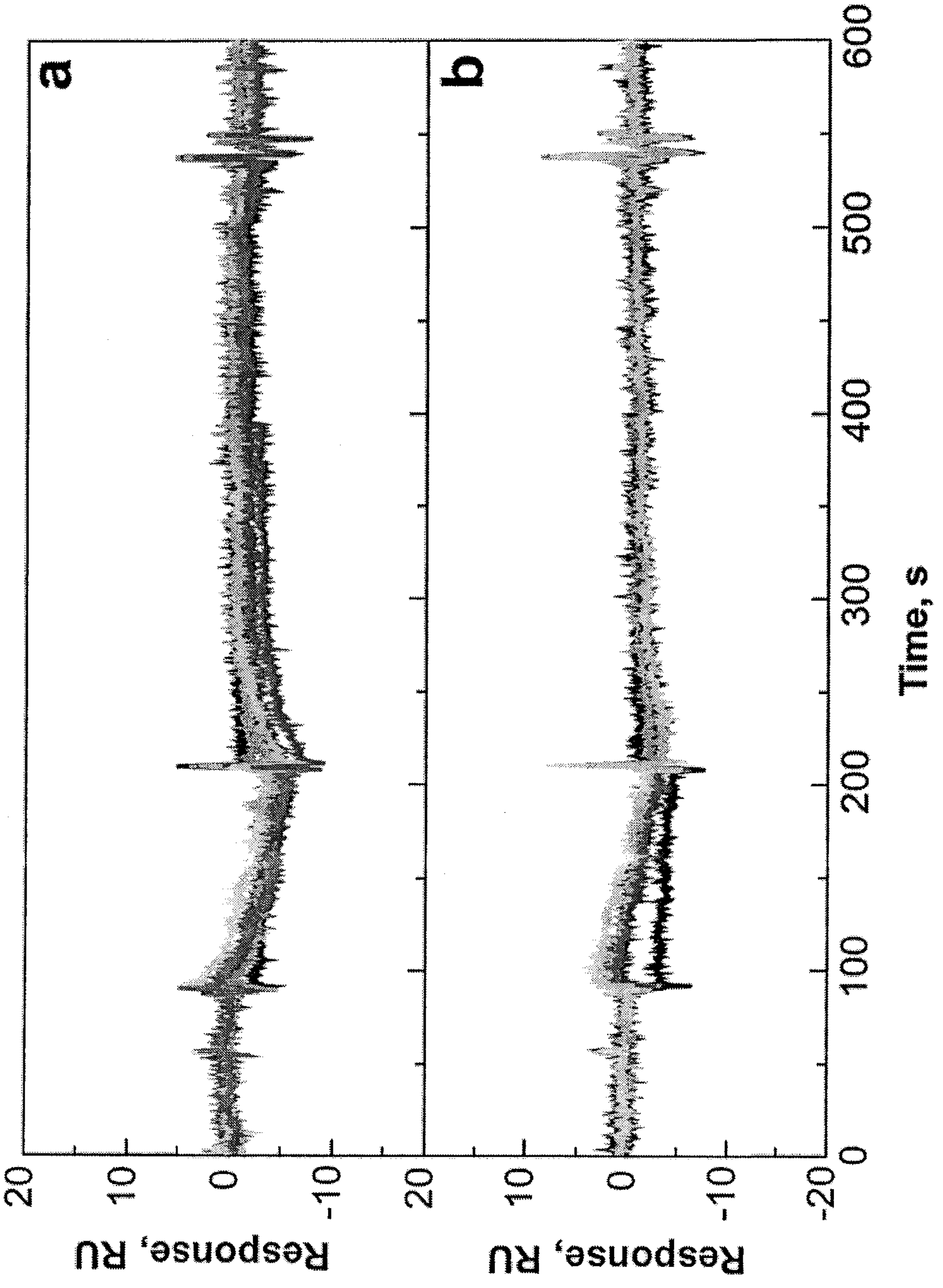
FIG. 8 shows an overlay plot of SPR biosensor sensorgrams illustrating that the Type II TGF-beta receptor does not bind to immobilized P3378 (FIG. 8A) or P3375 (FIG. 8B), as evidenced by the lack of response (RUs).

FIG. 8 presents SPR biosensor sensorgrams showing the interaction of the extracellular domain of the Type II TGF-beta receptor (38 nM to 4.5 μM) with immobilized P3378 (500 RUs) (FIG. 8A) or P3375 (1200 RUs) (FIG. 8B). In both cases no significant signal was observed, indicating that the Type II TGF-beta receptor does not interact with these peptides.

Figure 9:
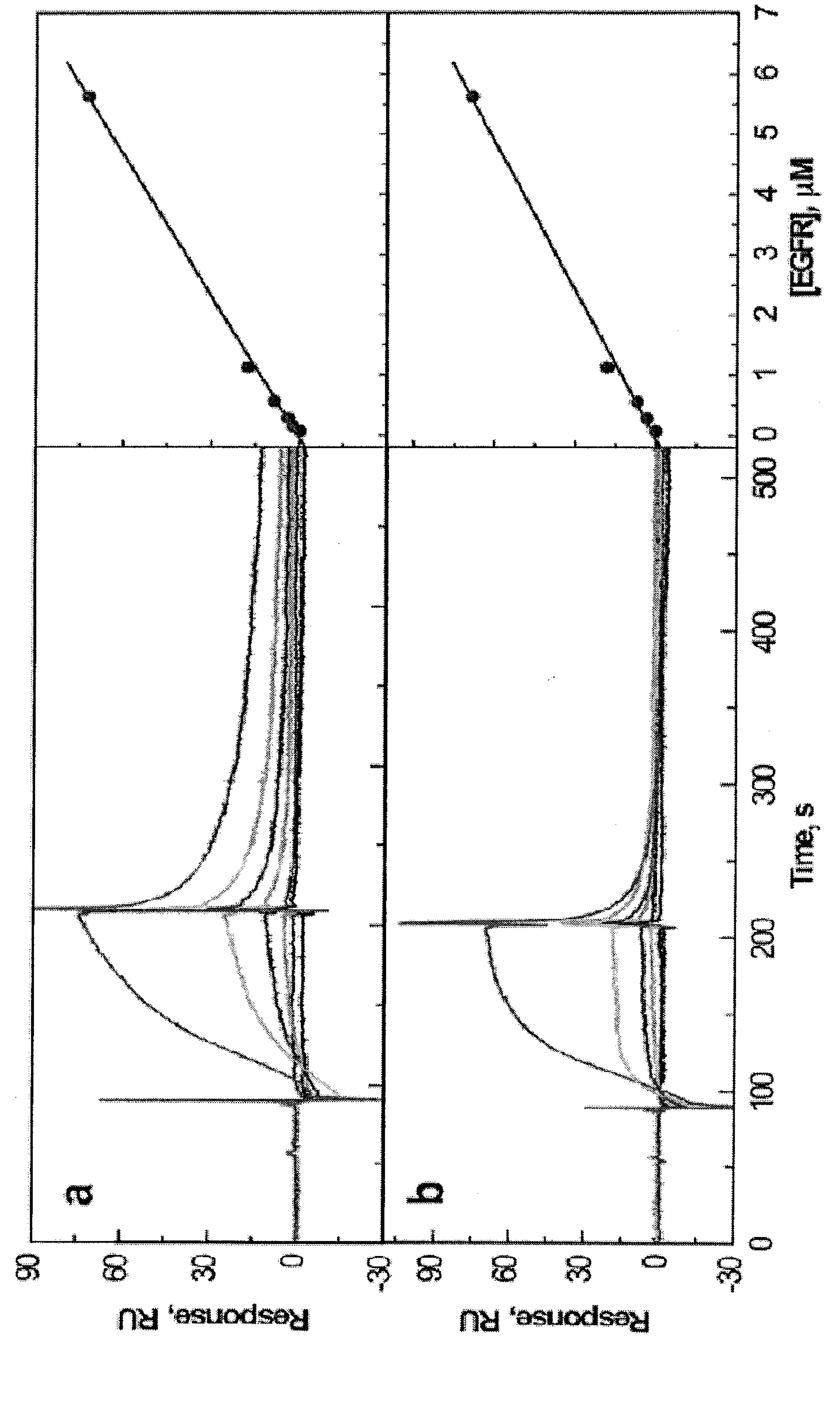
FIG. 9 shows overlay plots of SPR biosensor sensorgrams illustrating that the epidermal growth factor receptor does not bind to immobilized P3375 (FIG. 9A) or P3378 (FIG. 9B), as evidenced by linear Scatchard plots (right panels).

FIG. 9 shows an overlay plot illustrating the binding of the epidermal growth factor ectodomain (EGFR-ED) (70 nM to 5.63 μM) to immobilized P3375 (1200 RUs; FIG. 9A) or P3378 (500 RUs; FIG. 9B). The linear nature of the Scatchard plots (right panels) indicates that these peptides do not bind specifically to EGFR-ED.

In summary, the results in FIGS. 8 and 9 show that P3378 and P3375 do not interact specifically with proteins that are unrelated to clusterin, indicating that their binding to rh-clusterin is specific.

Example 6

Characterization of the Sequence Dependence of the Clusterin-Peptide Interactions The sequence dependence of the clusterin-peptide interactions was investigated using SPR biosensor analysis and peptides with scrambled sequences. Immobilization of the peptides on the sensor chips and the SPR experiments were conducted as described in Example 4.

Figure 10:
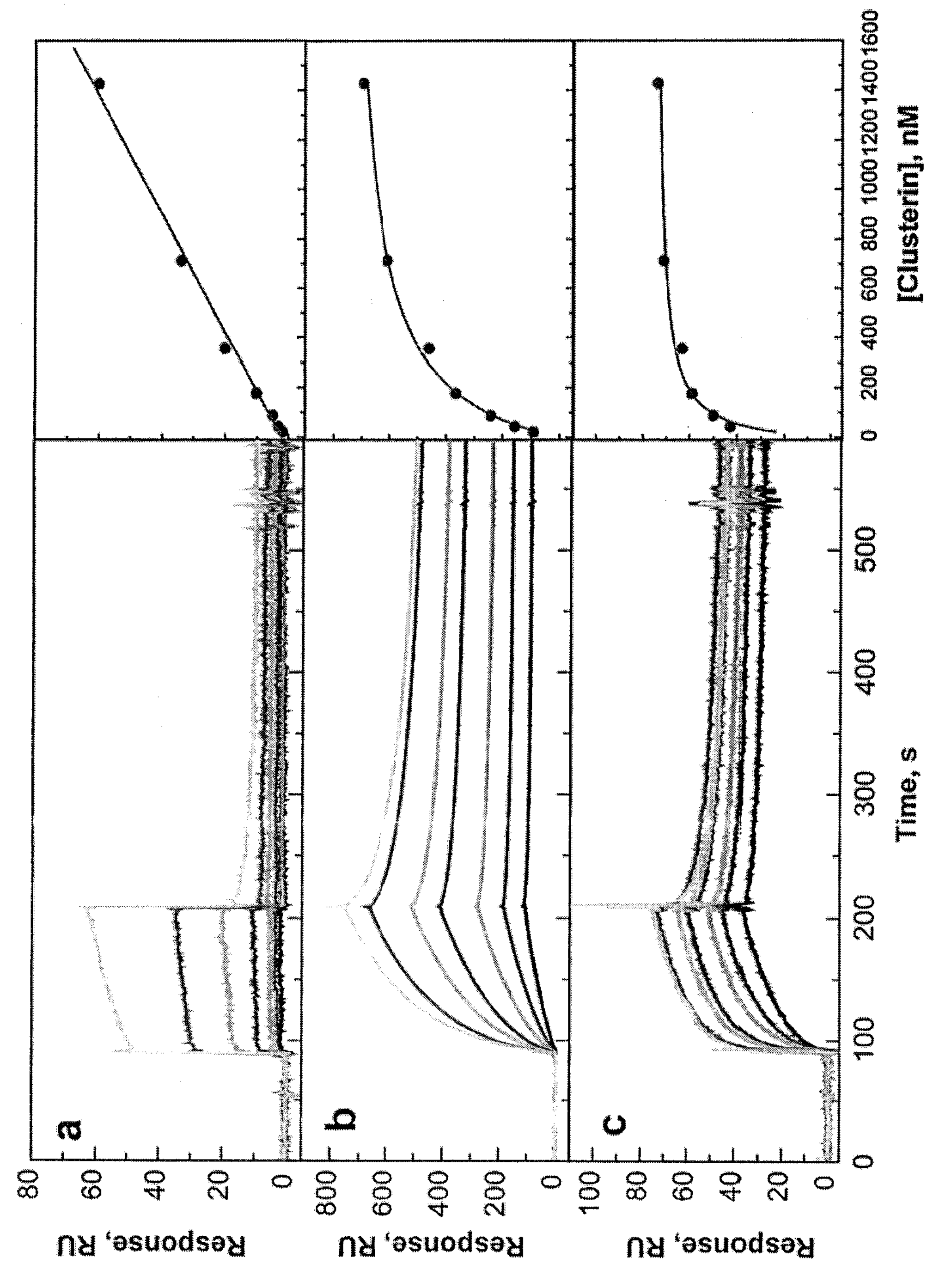
FIG. 10 shows overlay plots of SPR biosensor sensorgrams obtained when clusterin was flowed over immobilized peptides with randomized versions of the P3378 (P3378R.

FIG. 10 presents SPR biosensor sensorgrams showing the interaction of rh-clusterin (11 nM-1.4 μM) with immobilized randomized versions of the clusterin-binding peptides of the present invention: P3378R (PYLHQSPHWKPSSGSGC—SEQ ID NO:6), P3375R (LSLYHTNTQFWQSGSGC—SEQ ID NO:7), and P3376R (AWHTLASTSLAPSGSGC—SEQ ID NO:8). The fact that clusterin bound to P3375R (13850 RUs) and P3376R (3300 RUs) (FIGS. 10*b* and *c*, respectively), as evidenced by the curvilinear Scatchard plots (right panels), demonstrates that the binding of P3375 and P3376 to clusterin is not peptide sequence specific. The linear nature of the Scatchard plot for P3378R (3378 RUs) (FIG. 10*a*, right panel) confirms the sequence dependent nature of the interaction of P3378 with clusterin (also see FIG. 4).

Example 7

Characterization of P3378 Clusterin Epitope in Comparison to mAb 16B5

The question of whether an EMT-blocking anti-clusterin monoclonal antibody (mAb) 16B5 and P3378 have overlapping or independent binding sites on clusterin was investigated using SPR biosensor analysis. Several mAbs that interact with clusterin have been isolated; five of these mAbs, including 16B5, interact with an epitope on clusterin that is important for the EMT-promoting action of clusterin. Accordingly, these anti-clusterin mAbs inhibit EMT in cell culture, and tumor metastasis in animal models (O'Connor-McCourt et al, WO 2007/030930). Since clusterin-binding peptides can be used to non-invasively image clusterin-expressing tumors (primary tumors and metastases) in vivo, it is important to determine whether treatment with anti-clusterin mAbs may block peptide binding to the clusterin target and therefore compromise the ability of the peptides to image the tumor. Immobilization of the peptides on the sensor chips and the SPR experiments were conducted essentially as described in Example 4.

Figure 11:
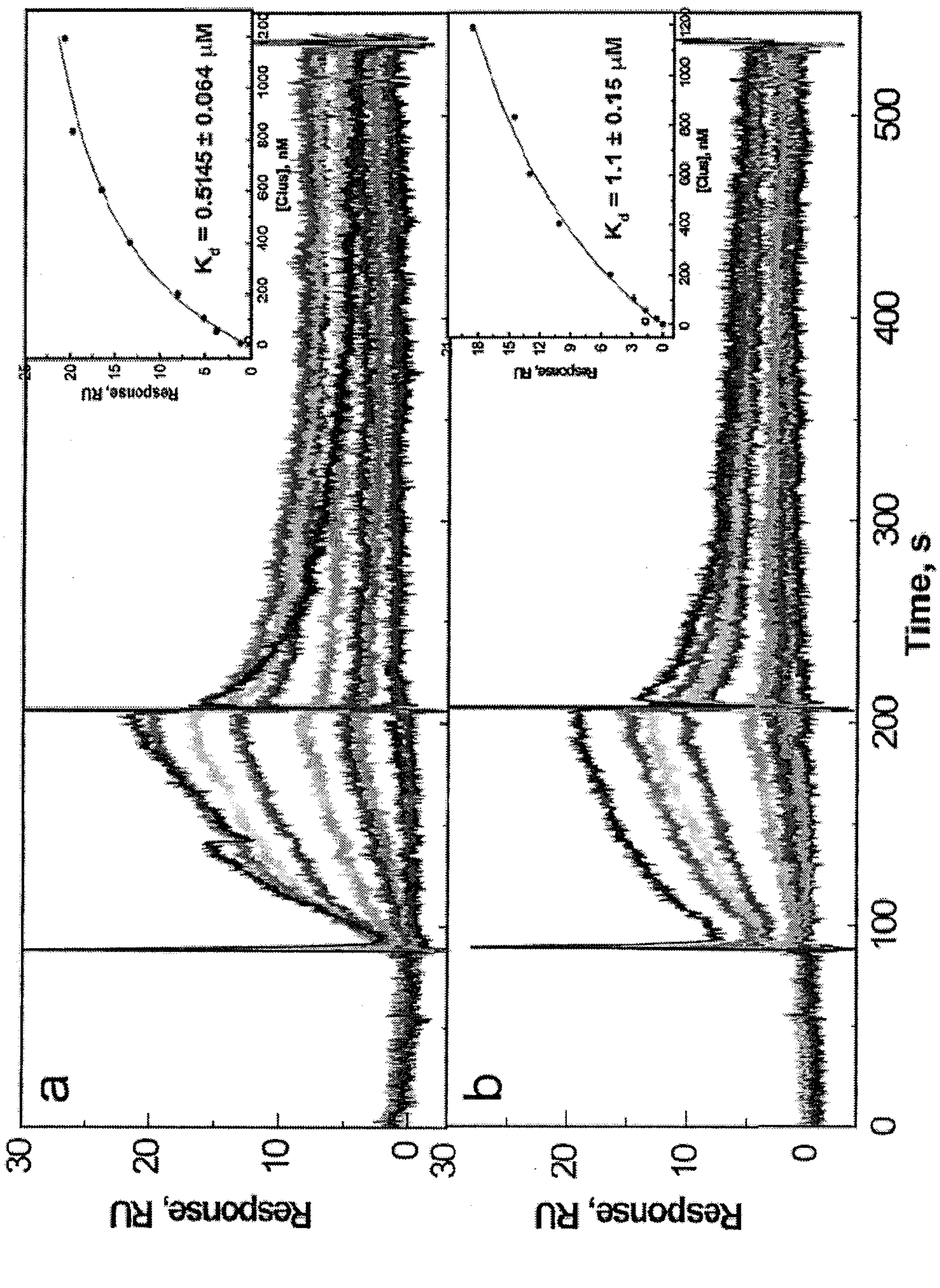
FIG. 11 shows overlay plots comparing binding sites on clusterin for P3378 and monoclonal Antibody 16B5.

FIG. 11 depicts an overlay plot of sensorgrams illustrating the binding of rh-clusterin to immobilized P3378 peptide in the absence and presence of 16B5 mAb. The injection of increasing concentrations of rh-clusterin (0-1.2 μM) over the immobilized P3378 peptide resulted in a $K_D$ of 0.52 μM (FIG. 11*a*). When rh-clusterin was preincubated with mAb 16B5 (ratios of 1:1.7) and then flown over the same peptide surface a $K_D$ of 1.1 μM was measured (FIG. 11*b*). These results show that the presence of mAb 16B5 did not significantly affect the binding affinity of rh-clusterin to immobilized P3378, indicating that mAb 16B5 and P3378 peptide bind to non-overlapping sites on rh-clusterin. Accordingly, P3378 should not be blocked from interacting with, and imaging, tumors that have been treated with 16B5 mAb.

Example 8

Clusterin Secretion in Murine 4T1 Mammary Tumor Cells

In order to demonstrate tumor imaging in animal models, it is essential to choose a tumor cell line (which will be implanted in the animal) that expresses the target, in this case clusterin. Therefore, it was demonstrated that murine 4T1 mammary tumor cells secrete clusterin and that the level of secreted clusterin correlates with the mesenchymal phenotype.

Murine 4T1 tumor cells were shown to produce the secreted form of clusterin, with this secretion being augmented by treatment with TGF-β (FIG. 12). Mouse mammary 4T1 tumor cells were obtained from ATCC and cultured according to their recommendations. When grown in the presence of TGF-β for 24 hrs, 4T1 mouse mammary tumor cells undergo a very subtle mesenchymal-like morphology change compared to the non-treated cells (CTL) (FIG. 12A). Western blot analysis of 50 μL of conditioned medium obtained from cells that were grown in the absence (CTL) or presence of TGF-β for 24 hrs indicates that clusterin secretion by the cells is increased by TGF-β (FIG. 12B). The lack of clusterin in the medium control (Med) indicates that the clusterin detected in the non-treated 4T1 cell conditioned media is not derived from the growth medium itself (DMEM+10% Fetal Bovine Serum (FBS)). These results show that clusterin is secreted by 4T1 cells and that the amount of secreted clusterin is increased by TGF-β, i.e. that the level of clusterin expression is correlated with a more mesenchymal phenotype. The motility of 4T1 cells is increased by the presence of TGF-β as shown in a wound healing assay (FIG. 12C), confirming the correlation between increased clusterin and the mesenchymal phenotype. Pictures were taken with a Nikon CoolPix 995 digital camera mounted on a Leitz Labovert inverted microscope.

Example 9

Imaging of 4T1 Tumor-Bearing Animals Using Labeled Clusterin-Binding Peptide (P3378)

Figure 16:
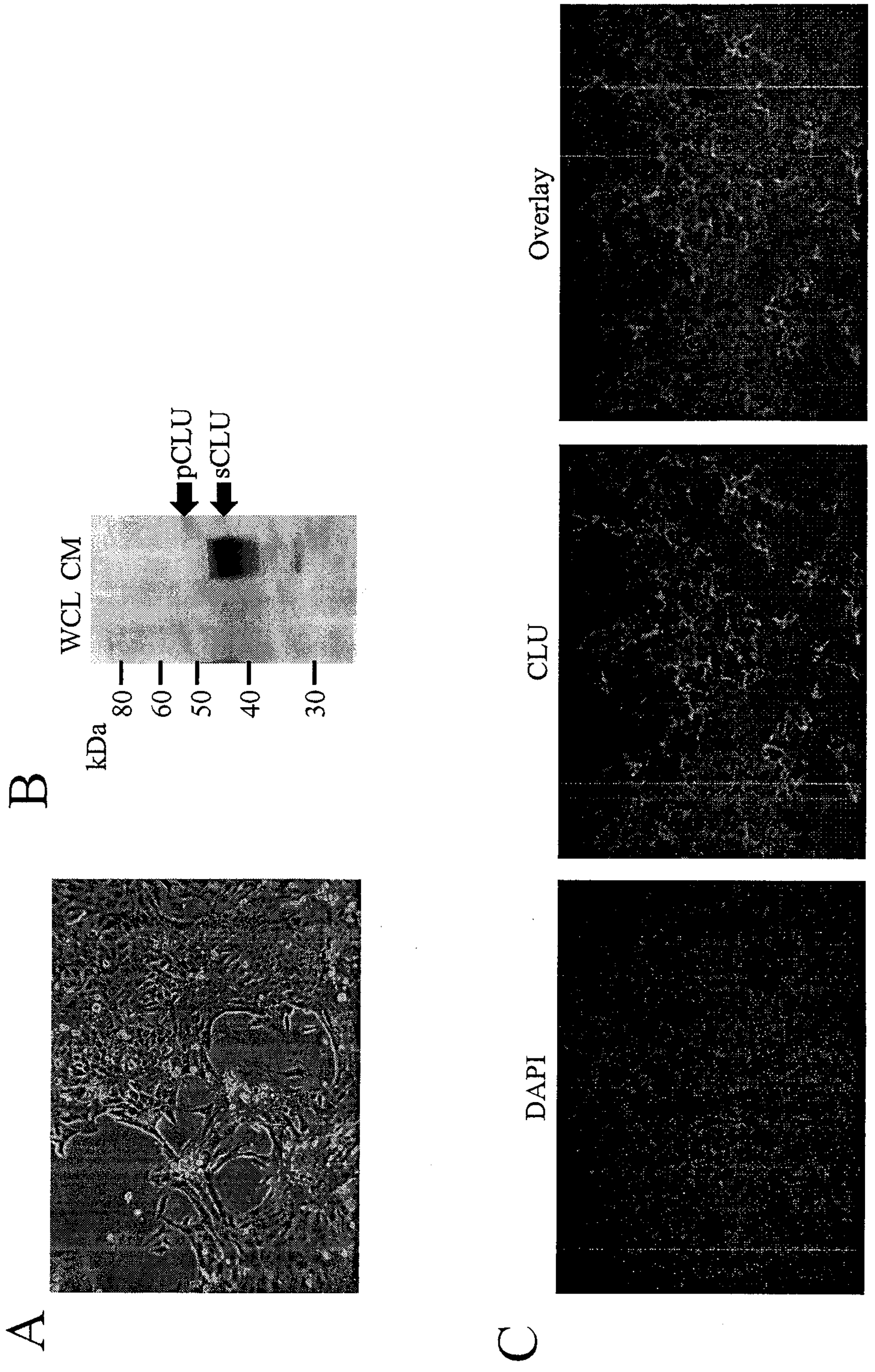
FIG. 16 shows that mouse mammary 4T1 tumor cells express and secrete clusterin.

In preparation for molecular imaging, the peptide P3378 (and its randomized control peptide, P3378R) were labeled with different probes. Alexa Fluor 680 C2-maleimide was purchased from Invitrogen Canada Inc. (Burlington, ON). Labeling of the P3378 and P3378R peptides with Alexa Fluor 680, Dylight 680 or Dylight 800 was performed according to the manufacturer's instructions (Molecular Probes). The Alexa Fluor 680-Peptide conjugate was generated by incubating a 3:1 (dye:peptide) molar ratio of 7.0 mM Alexa Fluor 680 C2 maleimide (dissolved in DMSO) with 0.3 mM of peptide in 50 mM phosphate buffer (pH 7.2) at 4° C. for 24 h in the dark. The crude conjugate was purified by use of analytical HPLC on a Vydac-C18 reversed-phase column, 4.6×250 mm, using a gradient of 0-60% (1%/min, flow rate 1.0 ml/min) acetonitrile in 0.1% TFA. The elution profile was monitored by absorbance at 278 nm. The identities of all purified labeled peptides were verified by electrospray mass spectrometry (ESI-MS). The peak containing the peptide-Alexa 680 conjugate was collected, lyophilized, redissolved in sterile saline at a concentration of 250 μM (determined spectrophotometrically using predicted extinction coefficients), and stored in the dark at −80° C. until use As a model system, 4T1 mouse mammary carcinoma cell line cells were used to generate tumors in syngeneic BALB/c mice. 4T1 cells have been shown to express and secrete significant amounts of clusterin (FIG. 16 and Lenferink 2009) and provide a syngeneic in vivo model system when injected in female BLAB/c animals. All animal procedures were done in compliance with institutional guidelines and according to protocol 08-MAR-I-12 approved by the Animal Care Committee in the Biotechnology Research Institute of the National Research Council of Canada, (Montreal QC). Six to eight weeks old female BALB/c mice were obtained from Charles River. High concentration phenol-red-free Matrigel free of Lactose Dehydrogenase Elevating Virus was purchased from Becton Dickinson (Franklin Lakes, N.J.). A 50 μl 1:1 solution of sterile Matrigel and saline, or the same solution containing 4T1 mouse mammary tumor cells ($5\times10^6$ cells), was injected subcutaneously into the right hind thigh of the animal. Clippers and Nair were used to remove hair from the injection site as well as the lower back and the left thigh of the animals prior to the Matrigel and tumor cell injections. When tumors measured ~0.5 to 0.8 cm in diameter (6-8 days), the tumor-bearing mice were subjected to in vivo imaging.

For immunofluorescent microscopy, OCT embedded 4T1 tumors were sectioned using a Leica CM1900 cryostat (Leica, Richmond Hill, ON, Canada) at 8 μm thickness and placed on Superfrost Plus microscope slides (Fisher Scientific, Ottawa, ON, Canada) and kept at −80° C. until use. Frozen sections were air dried, fixed for 5 minutes in 10% buffered-formalin and non-specifically blocked for 5 min at room temperature with Ultra V Block (Thermo Fisher Scientific, Nepean, ON, Canada). Slides were then incubated overnight at 4° C. with clusterin antibody M-18 (1:100; Santa Cruz Biotechnology, Santa Cruz, Calif., USA) and then subjected to a secondary Alexa Fluor 555-labeled donkey-anti-goat IgG (1:200; Invitrogen, Burlington, ON, Canada) for 30 min at room temperature. Nuclei were counterstained with 4,6-diamidino-2-phenylindole (DAPI) at 0.1 μg/ml in PBS for 1 min at room temperature. All washing steps used PBS, except the last step, which used water. Finally, slides were mounted using ProLong Gold Antifade™ (Invitrogen, Burlington, ON, Canada). Fluorescence was detected with a Leitz Aristoplan™ microscope (Thermo Fisher Scientific, Nepean, ON, Canada) coupled to a QImaging™ Retiga-2000R CCD camera (QImaging, Surrey, BC, Canada), analyzed using QCapture™ software (Meyer Instruments, Houston, Tex., USA), and subsequently pseudo-colored with Photoshop (Adobe Systems, Toronto, ON, Canada).

For near-infrared fluorescent microscopy, after completion of in vivo tumor targeting experiments, animals were perfused with heparinized saline, their brain dissected and then frozen on dry ice. Mouse brain tissues were embedded in Tissue-Tek™ freezing medium and sectioned on a cryostat at 10 μm thickness, then mounted on Superfrost™ Plus microscope slides (Fisher Scientific, Nepean, ON, Canada). Frozen tissue sections were fixed in methanol for 10 min at room temperature. Slides were rinsed with 0.2 M PBS (pH 7.3), followed by incubation with 5% donkey serum in PBS for 1 hour with 0.1% Triton™-X 100 at room temperature. After blocking, slides were incubated with goat anti-mouse clusterin primary antibody (1:100) for 1 hour at room temperature followed by Alexa 568-labeled donkey anti-goat secondary (1:500; Molecular Probes) for 1 h at room temperature. Slides were again washed with PBS five times, then dried of excess liquid and cover slipped using DAKO fluorescent mounting media containing Hoechst (1:1000). Images were captured using Olympus 1X81 inverted motorized microscope (Markham, Ontario, Canada) and analyzed using ImagePro™ 6.2 (Markham, Ontario, Canada).

Animals were imaged using the following procedures. Animals were anesthetized using isoflurane (3% in $O_2$ at 2 L/min). Prior to the injection of the labeled peptides, animals were subjected to a full body scan to obtain a background fluorescence image. P3378-Alexa680 or P3378R-Alexa680 was administered (25 nmol in 100 μL sterile saline) via the tail vein using a 0.5-ml insulin syringe with a 27-gauge fixed needle. Immediately after, the animal was placed on the heated animals plate (39° C.) of the ART eXplore Optix MX2 imaging system (Advanced Research Technologies, Montreal, Canada). Laser power and counting time per pixel were optimized at 9.6 μW and 0.5 s, respectively. These values remained constant during the entire experiment. The raster scan interval was set at 1.5 mm and was held constant during the acquisition of each image. The data were recorded as Temporal Point-Spread Functions (TPSF), and fluorescence intensity and fluorescence lifetime maps were generated. All images were analyzed using the ART Optix OptiView™ software. Volume data and 3D images were reconstructed using the ART OptiView™ 3D Reconstruction Software Module. All animals were euthanized after the imaging experiments.

Animals were imaged in the ART Optix MX2 small animal imager using three approaches:

a. Mice were injected intravenously (i.v.) via the tail vein with either 5 nanomoles of P3378 peptide labeled with Alexa680, or P3378R peptide labeled with Alexa680;
b. Mice were injected intravenously (i.v.) via the tail vein with either 25 nanomoles of P3378 peptide labeled with Alexa680, or P3378R peptide labeled with Alexa680;

c. Mice were co-injected i.v. (tail vein) with a mixture of 25 nanomoles P3378 peptide labeled with the Dylight680 and 25 nanomoles P3378R peptide labeled with Dylight800 dye.

Since in the first two approaches (a, b) the clusterin-binding peptide and control peptide were labeled with the same fluorophore, the homing ability of each peptide had to be monitored individually, i.e. at different times and/or in different animals. The differential labeling of the clusterin-binding peptide and the control peptide in the third approach (c) allowed for co-injection and the near simultaneous monitoring of the ability of these two peptides to home to the same 4T1 tumor in the same mouse. The switch from the Alexa labeling used in the first two approaches to the DyLight™ labeling used in the third approach was made in order to be able to use two different fluorophores, and also because in many applications the DyLight™ Dyes have been shown to exhibit a higher fluorescence intensity and photostability than the Alexa fluorophors.

In the initial experiments (a, b), one animal received an injection of P3378-Alexa680 on one day after which imaging data was collected for 3 hrs post-injection. Twenty-four hrs post-peptide injection, this animal was re-scanned (using the same parameters as the previous day) to confirm that P3378-Alexa680 was cleared from the mouse. Then the P3378R-Alexa680 scrambled peptide was injected and the same measurements were carried out as the day before. Using this set-up, the behavior of the two peptides was compared in the same animal on the same tumor, but on different days.

Either 5 nanomoles or 25 nanomoles of labeled peptide in 100 μL of saline was injected. This corresponded to initial circulating peptide concentrations of ~3 μM and ~15 μM respectively. Clusterin is a mid-abundant circulating protein present in blood (100 μg/ml=~1 μM). Since the initial concentration of injected peptide was higher than the concentration of circulating clusterin when injecting either 5 or 25 nanomoles of peptide, free circulating peptide (non-clusterin bound) should be available to home to tumors in both cases. Using the ART Optix MX2 small animal imager, an accumulation of both P3378-Alexa680 and P3378R-Alexa680 in the tumor (as well as in the kidney and bladder) at both peptide concentrations was observed.

Importantly, the P3378-Alexa680 peptide cleared more slowly from the tumor site than the P3378R-Alexa680 peptide, indicating that the P3378 peptide was selectively retained at the tumor site due to clusterin binding (FIG. 13A). This effect correlated with a faster accumulation of the P3378R scrambled peptide in the kidneys, which may reflect a "tumor antigen sink" effect, i.e. since less P3378R scrambled peptide is retained in the tumor, more remains in the circulation and is available for clearance in the kidney (FIG. 13B). These results indicate that the P3378 has specificity for the clusterin secreted by the 4T1 tumor cells.

To obtain further conclusive data with regard to the specificity of the tumor targeting ability of the P3378 peptide, a third approach (c) was used, in which the P3378 peptide was labeled with a Dylight680 and the P3378R peptide was labeled with a Dylight800 fluorophor. A 1:1 mixture of both peptides (25 nanomoles each) was then injected i.v. in 4T1 tumor-bearing BALB/c mice (as described above). In addition, these same animals were also injected on the left thigh (s.c.) with the vehicle in which the 4T1 cells were injected (50 μL Matrigel/saline, 1:1 (v/v)). This allowed monitoring of the homing behavior of both peptides at the tumor site (right thigh) and the vehicle control site (left thigh) in the same mouse, at virtually the same time.

Figure 14:
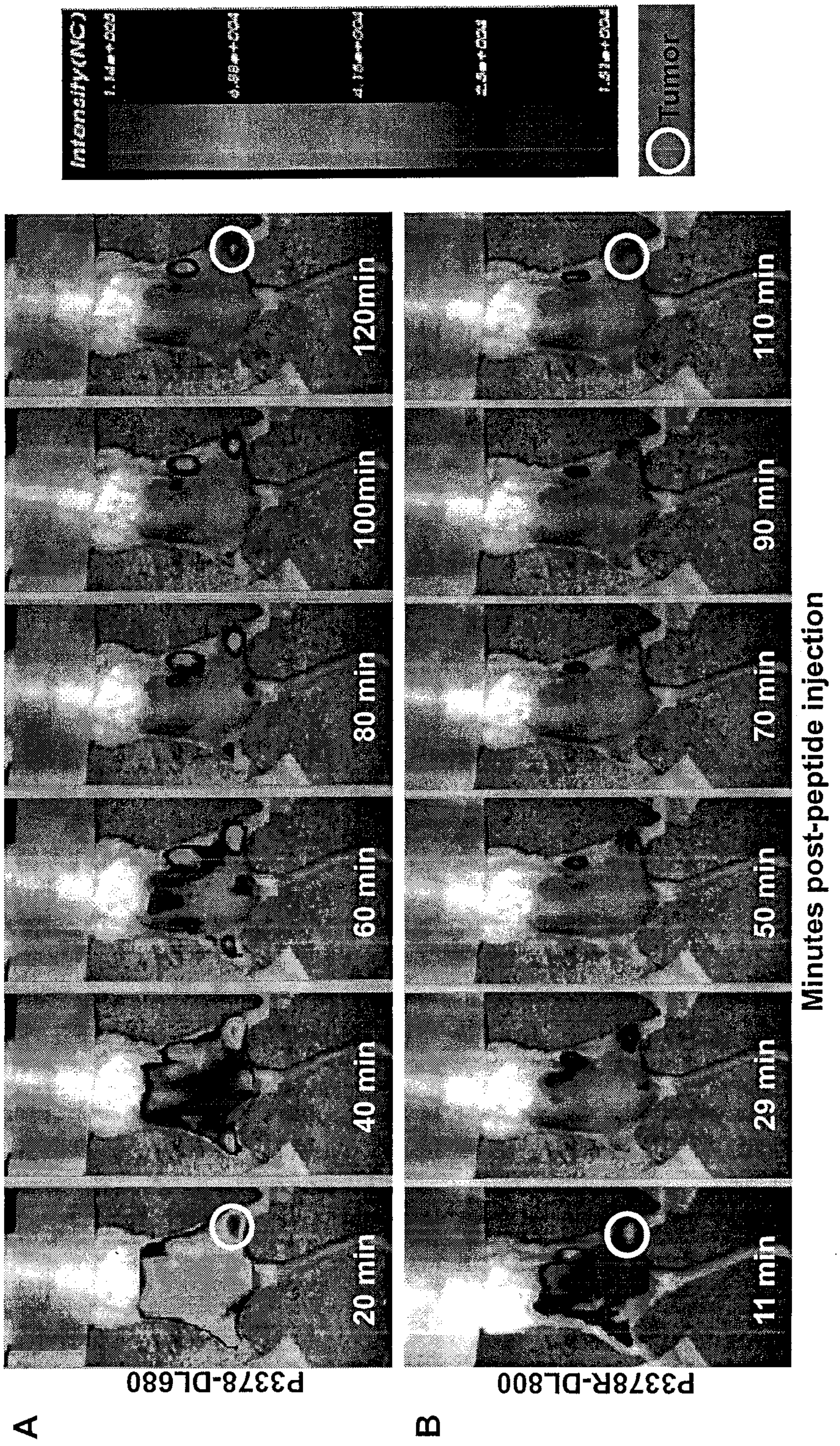
FIG. 14 shows representative images of the time-dependant fluorescence intensity maps which follow the distribution in 4T1 tumor bearing mice of the clusterin binding peptide P3378 labeled with the DyLight680 (P3378R-DL680) fluorophor (FIG. 14A), or the scrambled control peptide P3378R labeled with the DyLight™800 (P3378RDL800) fluorophor (FIG. 14B), from 11 to 110 (P3378-DL680) or 20 to 120 (P3378R-DL800) min post-peptide injection.
Figure 17:
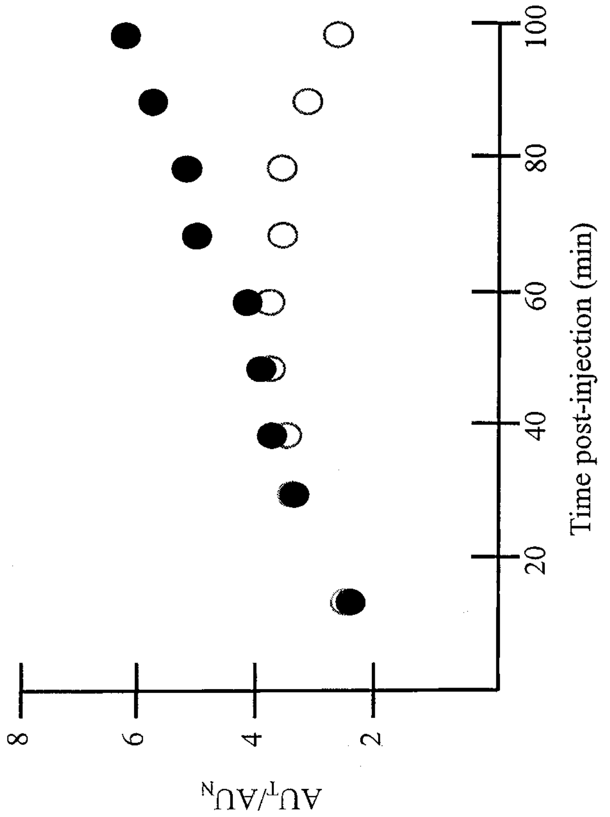
FIG. 17 depicts a graph plotting of the average fluorescence intensity (AU) for a region of interest (ROI) of the tumor (AUT) and the non-tumor containing contra-lateral side (AUN) shows a similar tumor accumulation of both peptides up to ~60 min post-injection, after which the P3378R peptide is cleared from the tumor while the P3378 peptide is retained.

The results from these experiments, in which 6 animals were used, confirmed those obtained in the previous experiments (a and b, above). FIG. 14 shows that the P3378 peptide resided much longer at the tumor site as compared to the P3378R peptide, thereby confirming the specificity of the P3378 peptide for tumor targeting. This observation was further confirmed by determining the tumor signal-to-background ratio over time for both peptides (FIG. 17). To do so, the average fluorescence intensity (AU) was determined for a region of interest (ROI) that was drawn around the tumor ($AU_T$) and the non-tumor containing contra-lateral side ($AU_N$) of the same animal. Plotting the $AU_T/AU_N$ ratios as a function of time shows that both peptides initially accumulate at the tumor site at the same rate up to ~60 min post-injection, after which the P3378R peptide is cleared from the tumor while the P3378 peptide remains at the tumor site.

Figure 15:
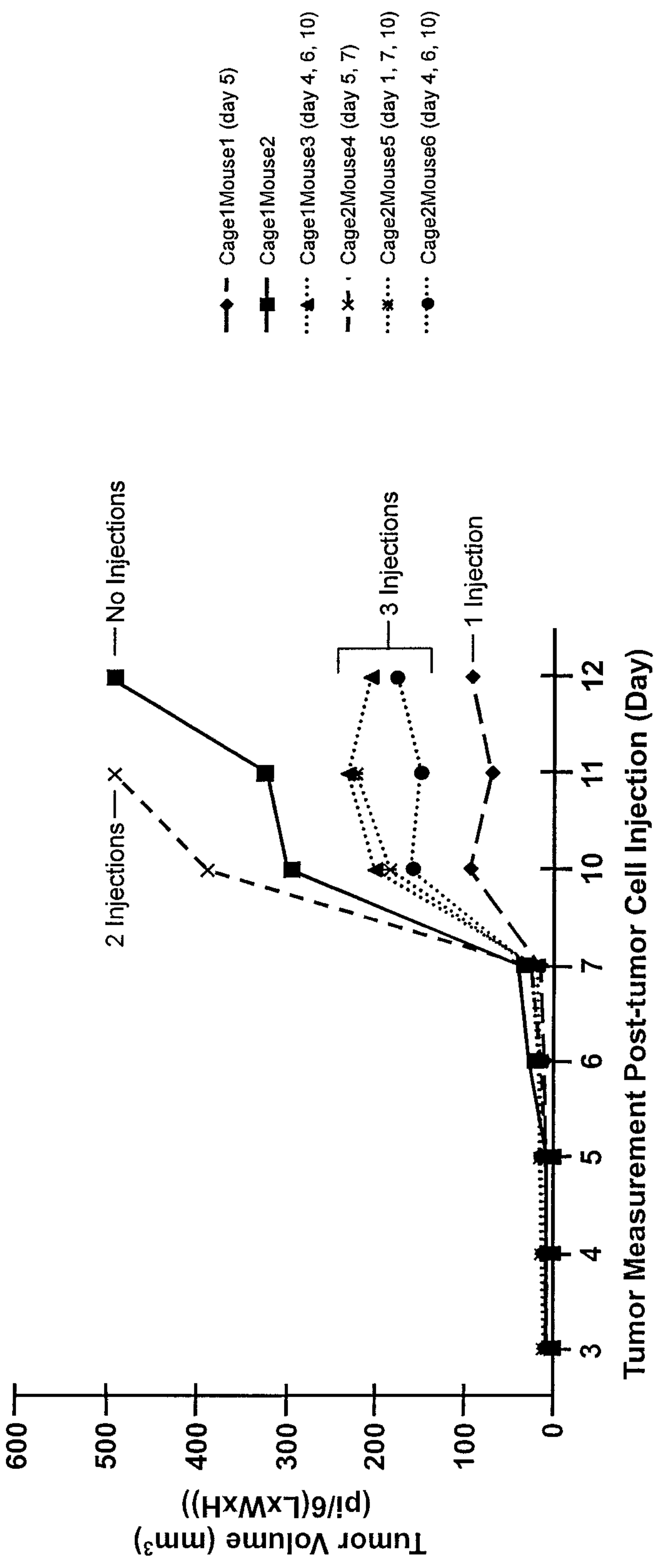
FIG. 15 is a graph showing the increase in tumor volume calculated from the obtained tumor measurements (p1/6 (Length×Width×Height)) in 4T1 tumor bearing mice that have been exposed to P3378 and P3378R peptides.

During the course of these experiments it was also noticed that the tumors in the three animals injected with the P3378/P3378R peptide mixture tended to show a reduced growth rate over time (FIG. 15), indicating that these peptides may have anti-tumor effects. It should be noted that up to day 7 post-tumor cell injection the tumor size was measured in 2 dimensions (Length and Width, Height was set at 1 mm to be able to use the same formula throughout the experiments).

Figure 18A:
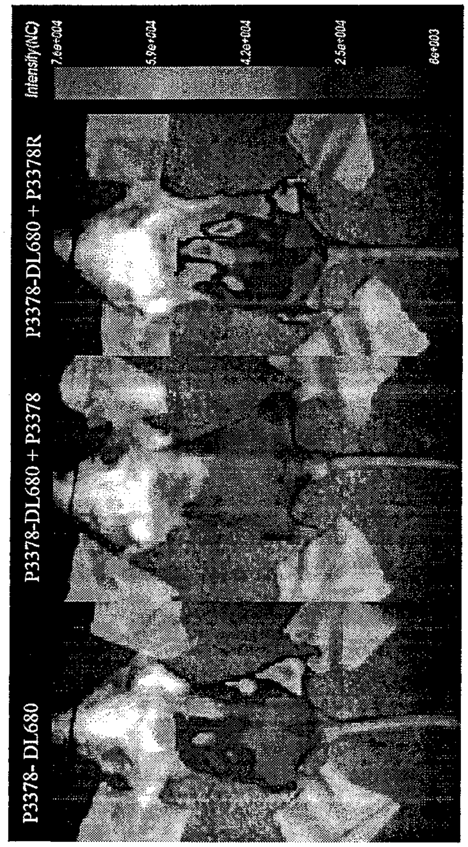
FIG. 18A shows tumor specific accumulation of P3378-DL680 (25 nmoles, left panel) determined 15 min post-injection is shown to be blocked by co-injection of excess unlabeled P3378 (middle panel) but not P3378R peptide (right panel).
Figure 18B:
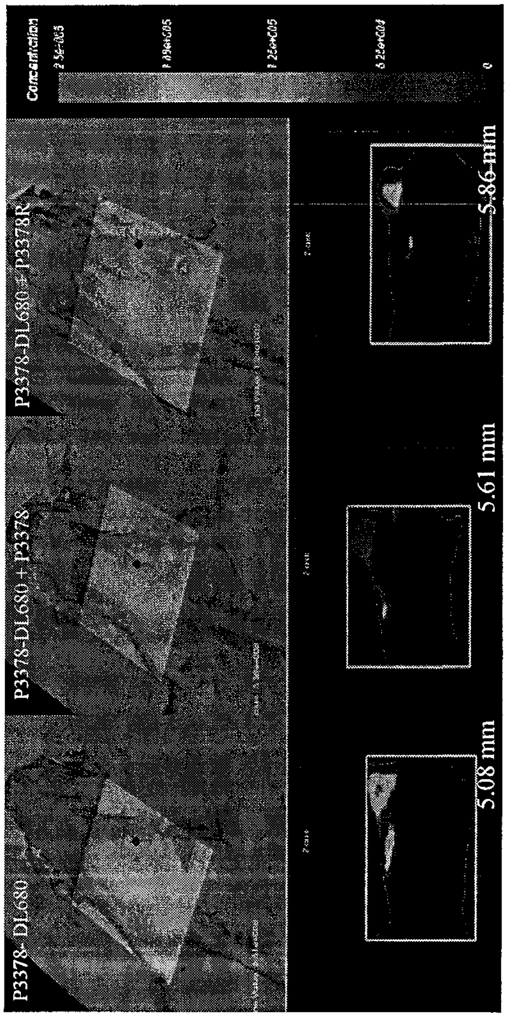
In FIG. 18B, determination of the relative concentration of P3378-DL680 at the tumor site (indicated with a white arrow) shows that this value is ~3-4 times lower in the presence of excess unlabeled P3378 (middle panel) whereas excess of unlabeled P3378R (right panel) only has a slight effect compared to the mouse injected with P3378-DL680 alone (left panel).

To further validate the specificity of the in vivo targeting ability of the P3378-DL680 probe, a blocking experiment using an excess of unlabeled P3378 peptide was carried out. Mice received 25 nmoles of P3378-DL680 alone (n=1) or in combination with 5 μmoles unlabeled P3378 or P3378R peptide (both n=2) in 100 μL sterile saline. Animals in the control groups received 25 nmoles of P3378-DL680 with or without 5 μmoles of the unlabeled scrambled P3378R peptide, whereas the experimental animals were injected with 25 nmoles of P3378-DL680 in combination with 5 μmoles of unlabeled P3378 peptide. As shown in FIG. 18A (15 min post-injection), unlabeled P3378 peptide successfully blocked uptake of the P3378-DL680 into the tumor whereas the unlabeled scrambled P3378R did not. Furthermore, using the gated NIRF lifetime and the OptiView 3D reconstruction module we selected in each mouse the slice along the Z-axis that contained the highest concentration of P3378-DL680 and determined its relative concentration. FIG. 18B shows that the relative concentration of the P3378-DL680 probe (FIG. 18B, middle panel) is ~3-4 times lower in the presence of excess unlabeled P3378 peptide, whereas this value was only slightly affected by the presence of excess of the scrambled P3378R peptide (FIG. 18B, right panel) compared to the P3378-DL680 injected animal (FIG. 18B, left panel).

Confocal microscopy was used to evaluate the distribution of the P3378-DL680 probe in the 4T1 tumor and various organs (liver, spleen, pancreas, kidney, heart, lungs), harvested 15 min post-injection. Frozen sections (10 μm thick) of the 4T1 tumor and organs harvested from an animal 15 min post-injection of P3378-DL680 (25 nmoles) show specific uptake and accumulation of the fluorescent probe in the 4T1 tumor, where it is co-localized with its target CLU. The P3378 peptide could not be detected in the other organs despite the presence of sCLU, which confirms on a microscopic level that the P3378-DL680 peptide is selectively taken up by the tumor. DAPI staining of the nuclei was used to visualize tissue morphology.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein are hereby incorporated by reference.

Berx G, Raspe E, Christofori G, Thiery J P, Sleeman J P. (2007) Pre-EMTing metastasis? Recapitulation of morphogenetic processes in cancer. *Clin. Exp. Metastasis.* 24: 587.

Cavanagh, et al. (1995) *Protein NMR Spectroscopy: Principles and Practice*. Elsevier Academic Press.

Gasteiger E. et al. (2005) Protein identification and analysis tools on the ExPASy Server. In: John M. Walker (ed): *The Proteomics Protocols Handbook*, Humana Press; 571-607.

Gupta G P, Massague J. (2006) Cancer metastasis: building a framework. *Cell.* 127: 679.

Lau S H, Sham J S, Xie D, Tzang C H, Tang D, Ma N, Hu L, Wang Y, Wen J M, Xiao G, Zhang W M, Lau G K, Yang M, Guan X Y. (2006) Clusterin plays an important role in hepatocellular carcinoma metastasis. *Oncogene.* 25: 1242.

Lenferink A E G, Cantin C, Nantel A, Wang E, Durocher Y, Banville M, Paul-Roc B, Marcil M, Wilson M R & O'Connor-McCourt M D (2009) Transcriptome Profiling of a TGF-beta-induced Epithelial-to-Mesenchymal Transition Reveals Extracellular Clusterin as a Target for Therapeutic Antibodies. *Oncogene.*

Massague J. TGFbeta in Cancer. (2008) *Cell.* 134: 215.

Mayer M, Meyer. (1999) Characterization of ligand binding by saturation transfer difference NMR spectroscopy. *Angew Chem, Int Ed.* 38:1784-1788.

Mayer M, Meyer B. (2001) Group epitope mapping by saturation transfer difference NMR to identify segments of a ligand in direct contact with a protein receptor. *J. Am. Chem. Soc.* 123: 6108-6117.

McCormack E, Micklem D R, Pindard L E, Silden E, Gallant P. Belenkov A, Lorens J B, Gjertsen B T. (2007) In vivo optical imaging of acute myeloid leukemia by green fluorescent protein: time-domain autofluorescence decoupling, fluorophore quantification, and localization. *Mol. Imaging.* 6:193.

Mourra N, Couvelard A, Tiret E, Olschwang S, Flejou J F. (2007) Clusterin is highly expressed in pancreatic endocrine tumours but not in solid pseudopapillary tumours. *Histopathology.* 50: 331.

Peng L, Liu R, Andrei M, Xiao W, and Lam K S. (2008) In vivo optical imaging of human lymphoma xenograft using a library-derived peptidomimetic against L4i.1 integrin. *Mol. Cancer Ther.* 7: 432.

Rosenthal E L, Kulbersh B D, King T, Chaudhuri T R, and Zinn K R. (2007) Use of fluorescent labeled anti-epidermal growth factor receptor antibody to image head and neck squamous cell carcinoma xenografts. *Mol. Cancer Ther.* 6:1230.

Steinberg J, Oyasu R, Lang S et al. (1997) Intracellular levels of SGP-2 (Clusterin) correlate with tumor grade in prostate cancer. *Clin. Cancer Res.;* 3:1707.

Su Z, Vinogradova A, Koutychenko A, Tolkatchev D, and Ni F. (2004) Rational design and selection of bivalent peptide ligands of thrombin incorporating P4-P1 tetrapeptide sequences: from good substrates to potent inhibitors. *Protein Eng. Des. Sel.* 17: 647-657

Wagnieres G A, Star W M and Wilson B C. (1998) In Vivo Fluorescence Spectroscopy and Imaging for Oncological Applications. *Photochemistry and Photobiology* 68:603.

Watari H, Ohta Y, Hassan M K, Xiong Y, Tanaka S, Sakuragi N. (2008). Clusterin expression predicts survival of invasive cervical cancer patients treated with radical hysterectomy and systematic lymphadenectomy. *Gynecol. Oncol.* 108: 527.

Zhang S, Zhang D, Zhu Y, Guo H, Zhao X, Sun B. (2006) Clusterin expression and univariate analysis of overall survival in human breast cancer. *Technol. Cancer Res. Treat.* 5: 573.

The invention claimed is:

1. An isolated or a synthesized peptide comprising the amino acid sequence as set forth in SEQ ID NO:1 or SEQ ID NO:2 or an amino acid sequence at least 80% identical to the amino acid sequence set forth in SEQ ID NO:1 or SEQ ID NO:2.

2. The isolated or synthesized peptide according to claim 1 linked to a cargo molecule.

3. The isolated or synthesized peptide according to claim 2, wherein the cargo molecule comprises an enzyme, an imaging moiety, a radioisotope or a cytotoxic agent.

4. The isolated or synthesized peptide according to claim 2, wherein the cargo molecule comprises an imaging moiety.

5. The isolated or synthesized peptide according to claim 4, wherein the imaging moiety comprises a radiolabel, a fluorophore, a near infrared fluorochrome or a magnetic nanoparticle.

6. A method of molecular imaging, diagnosis of a disease state in which clusterin is upregulated or treatment of a disease state in which clusterin is upregulated, the method comprising administering peptide having an amino acid sequence at least 80% identical to the amino acid sequence set forth in SEQ ID NO.:1 or SEQ ID NO.:2 to a subject in need of the imaging, diagnosis or treatment.

7. The method according to claim 6 further comprises molecular imaging of a tumor.

8. The method according to claim 7, wherein the molecular imaging is optical imaging, positron emission tomography, single photon emission computed tomography or magnetic resonance imaging.

9. The method according to claim 6, wherein the disease state is cancer.

10. A method of imaging a tumor comprising administering to a subject, a peptide comprising the amino acid sequence as set forth in SEQ ID NO.:1 or SEQ ID NO.:2 or an amino acid sequence substantially at least 80% identical to the amino acid sequence set forth in SEQ ID NO.:1 or SEQ ID NO.:2 linked to a cargo molecule, and detecting the imaging moiety in the subject.

11. An isolated or synthesized peptide comprising one, two or three conservative amino acid substitutions in the amino acid sec uence set forth in SEQ ID NO:1 or SEQ ID NO:2.

12. The isolated or synthesized peptide according to claim 1, comprising the amino acid sequence set forth in SEQ ID NO.:4.

13. The isolated or synthesized peptide according to claim 1, wherein the amino acid sequence has 85% sequence identity to SEQ ID NO:1 or SEQ ID NO:2.

14. The isolated or synthesized peptide according to claim 1, wherein the amino acid sequence has 90% sequence identity to SEQ ID NO:1 or SEQ ID NO:2.

15. The isolated or synthesized peptide according to claim 1, wherein the amino acid sequence has 95% sequence identity to SEQ ID NO:1 or SEQ ID NO:2.

16. The isolated or synthesized peptide according to claim 1, wherein the amino acid sequence has 100% sequence identity to SEQ ID NO:1 or SEQ ID NO:2.

17. A method of detecting tumor cells comprising administering to a subject in need thereof, an agent including a peptide comprising an amino acid sequence at least 80% identical to the amino acid sequence set forth in SEQ ID NO.:1 or SEQ ID NO.:2 linked to a cargo molecule, and detecting the agent, wherein said peptide is able to specifically bind clusterin.

18. The method of claim 17, wherein the peptide comprises the amino acid sequence set forth in SEQ ID NO: 1, SEQ ID NO: 2 or an amino acid sequence substantially identical thereto and the cargo molecule comprises an imaging moiety.

19. The method of claim 17, wherein the peptide consists in the amino acid sequence set forth in SEQ ID NO: 1 and the cargo molecule comprises an imaging moiety.

* * * * *

UNITED STATES PATENT AND TRADEMARK OFFICE

CERTIFICATE OF CORRECTION

PATENT NO. : 8,629,240 B2
APPLICATION NO. : 13/260676
DATED : January 14, 2014
INVENTOR(S) : Rana Filfil et al.

It is certified that error appears in the above-identified patent and that said Letters Patent is hereby corrected as shown below:

In the Specification

Column 4, lines 18-19, replace "(p1/6 (Length×Width×Height))" with....
"(pi/6 (Length×Width×Height))"

Signed and Sealed this
Third Day of June, 2014

Michelle K. Lee
*Deputy Director of the United States Patent and Trademark Office*